(12) United States Patent
Busch-Madsen et al.

(10) Patent No.: US 10,478,244 B2
(45) Date of Patent: *Nov. 19, 2019

(54) ELECTROSURGICAL PENCIL

(71) Applicant: CIMPAX APS, Slangerup (DK)

(72) Inventors: Michael Busch-Madsen, Brønshøj (DK); Patrick Busch-Madsen, Slangerup (DK)

(73) Assignee: CIMPAX APS, Slangerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/182,516

(22) Filed: Nov. 6, 2018

(65) Prior Publication Data

US 2019/0076184 A1  Mar. 14, 2019

Related U.S. Application Data

(62) Division of application No. 15/868,926, filed on Jan. 11, 2018, now Pat. No. 10,149,715, which is a (Continued)

(30) Foreign Application Priority Data

May 19, 2011  (DK) ................................ 2011 70251

(51) Int. Cl.
*A61B 18/00* (2006.01)
*A61B 18/14* (2006.01)

(52) U.S. Cl.
CPC ..................... *A61B 18/1477* (2013.01); *A61B 2018/00607* (2013.01); *A61B 2018/1412* (2013.01);
(Continued)

(58) Field of Classification Search
CPC ...... A61B 18/1477; A61B 2018/00607; A61B 2218/006; A61B 2218/008; A61B 2018/1412; F04C 2270/0421
See application file for complete search history.

(56) References Cited

U.S. PATENT DOCUMENTS 3,911,241 A  10/1975  Jarrard
4,619,258 A  10/1986  Pool
(Continued)

FOREIGN PATENT DOCUMENTS

AU    2008203348 A1    2/2009
CN     201150567 Y    11/2008
(Continued)

OTHER PUBLICATIONS

International Search Report, Application No. PCT/DK2012/050176, dated Jan. 2, 2013.
(Continued)

*Primary Examiner* — Scott M. Getzow
(74) *Attorney, Agent, or Firm* — Winston & Strawn LLP

(57) ABSTRACT

An extendable electrosurgical pencil adapted to receive an electrode controllable by an electrical signal for performing surgical operations, including a housing that comprises first and second housing parts with a main housing part therebetween, a flexible printed circuit, a switch on the main housing part that is adapted to be activated from outside the housing for closing the flexible circuit, and an electrode receiver on the first housing part, wherein the first housing part is adapted to slide inside the main housing part to provide a telescopic extension of the pencil, the electrode and the flexible printed circuit following the sliding movement.

19 Claims, 21 Drawing Sheets

Related U.S. Application Data division of application No. 14/487,447, filed on Sep. 16, 2014, now Pat. No. 9,901,391, which is a division of application No. 14/114,476, filed as application No. PCT/DK2012/050176 on May 18, 2012, now Pat. No. 8,858,550.

(52) U.S. Cl.
CPC ... *A61B 2218/006* (2013.01); *A61B 2218/008* (2013.01); *F04C 2270/0421* (2013.01)

(56) References Cited

U.S. PATENT DOCUMENTS

| | | | |
|---|---|---|---|
| 4,625,723 A | 12/1986 | Altnether et al. | |
| 5,098,430 A | 3/1992 | Fleenor | |
| 5,413,575 A | 5/1995 | Haenggi | |
| 5,693,044 A | 12/1997 | Cosmescu | |
| 6,099,525 A | 8/2000 | Cosmescu | |
| 6,361,532 B1 | 3/2002 | Burek | |
| 6,458,125 B1 * | 10/2002 | Cosmescu | A61B 18/042 606/31 |
| 2003/0233087 A1 | 12/2003 | Chen et al. | |
| 2005/0107777 A1 | 5/2005 | West, Jr. et al. | |
| 2006/0178667 A1 | 8/2006 | Sartor et al. | |
| 2006/0264928 A1 | 11/2006 | Kornerup et al. | |
| 2007/0219551 A1 | 9/2007 | Honour et al. | |
| 2008/0287943 A1 * | 11/2008 | Weber | A61B 18/0218 606/41 |
| 2009/0062791 A1 | 3/2009 | Lee et al. | |
| 2009/0125023 A1 | 5/2009 | Stephen et al. | |
| 2009/0248012 A1 | 10/2009 | Maor et al. | |
| 2011/0092971 A1 | 4/2011 | Sartor et al. | |
| 2012/0203223 A1 | 8/2012 | Terry et al. | |

FOREIGN PATENT DOCUMENTS

| | | |
|---|---|---|
| GB | 2406793 A | 4/2005 |
| WO | 00/28908 A1 | 5/2000 |

OTHER PUBLICATIONS

European Search Report, Appl. No. EP 15176768.8, dated Mar. 1, 2016.
European Search Report, Appl. No. 17202740.1, dated May 23, 2018.
U.S. Appl. No. 14/114,476, Non-Final Rejection, dated Feb. 13, 2014.
U.S. Appl. No. 14/114,476, Notice of Allowance, dated Jun. 10, 2014.
U.S. Appl. No. 14/487,447, Non-Final Rejection, dated Jun. 8, 2017.
U.S. Appl. No. 14/487,447, Notice of Allowance, dated Oct. 16, 2017.
U.S. Appl. No. 14/487,447, Corrected Notice of Allowability, dated Oct. 19, 2017.
U.S. Appl. No. 15/868,926, Non-Final Rejection, dated May 29, 2018.
U.S. Appl. No. 15/868,926, Notice of Allowance, dated Aug. 16, 2018.

* cited by examiner

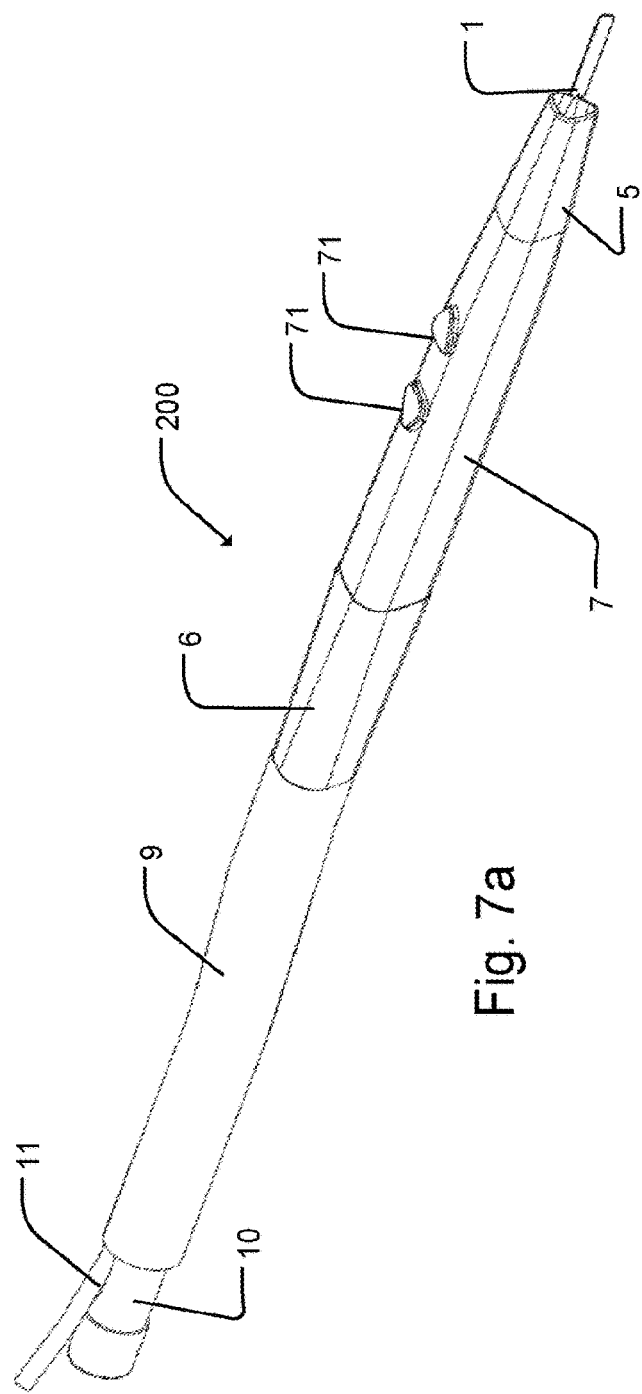
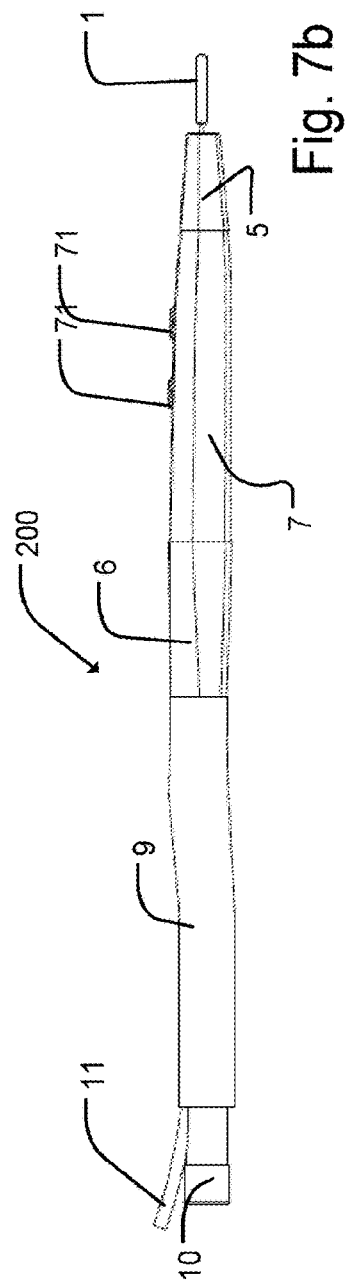
Fig. 7a
Fig. 7b

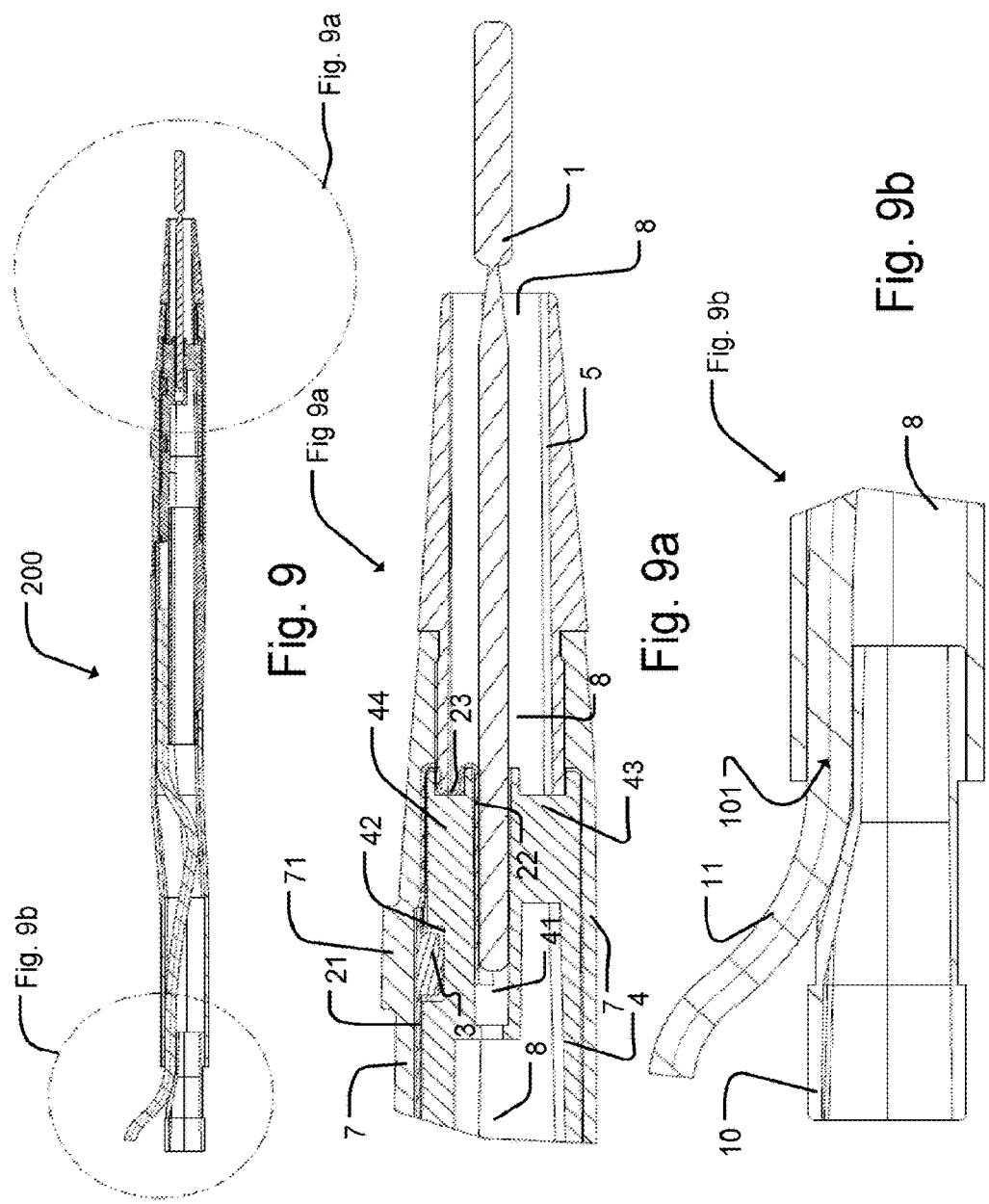

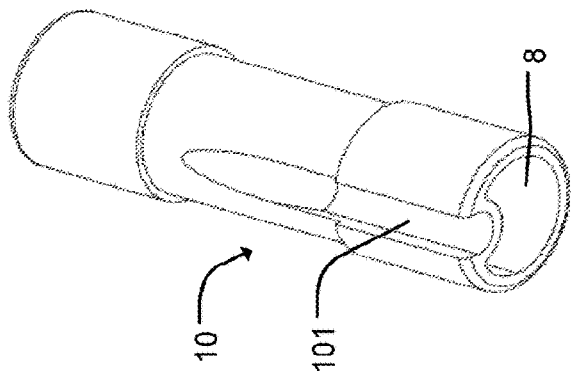
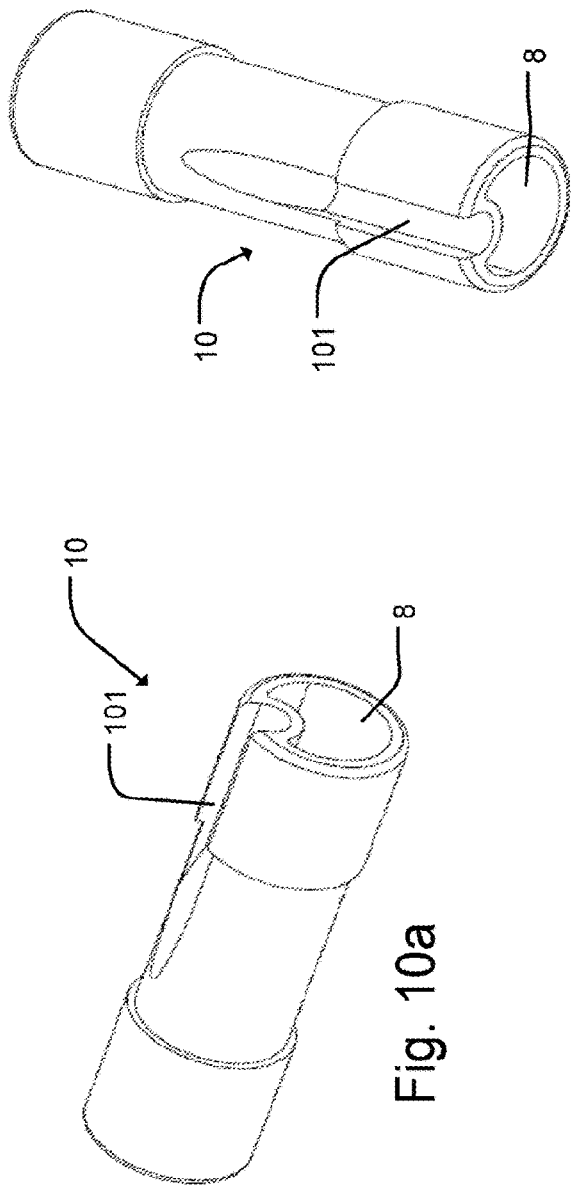
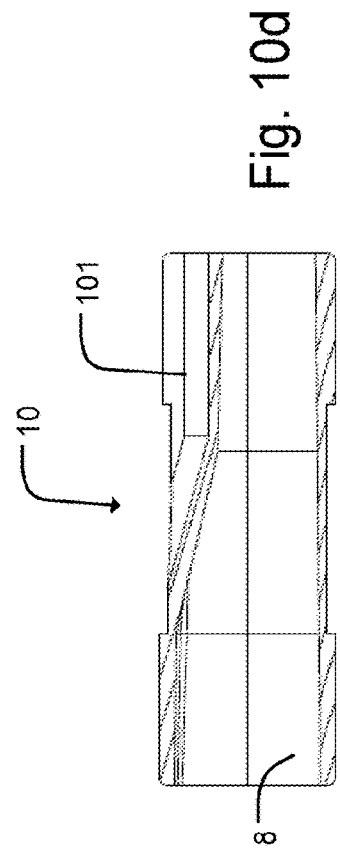

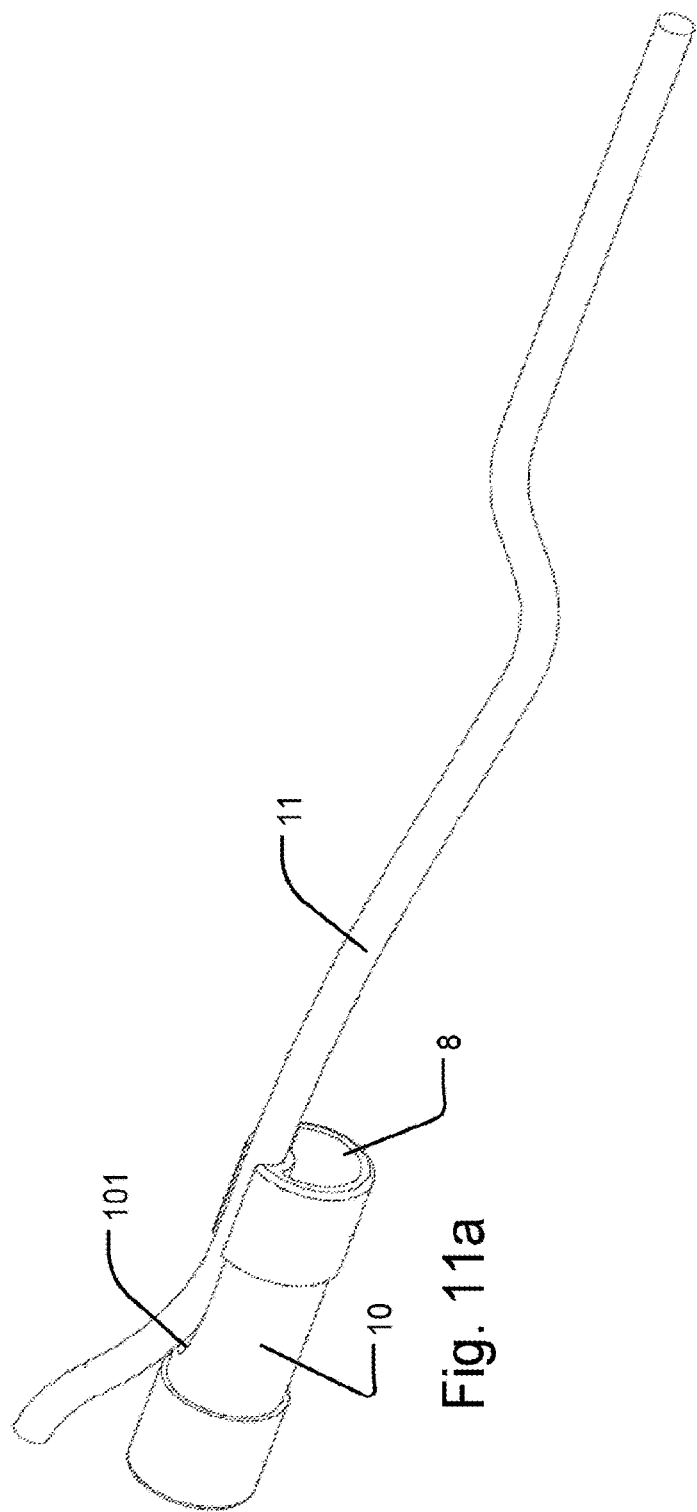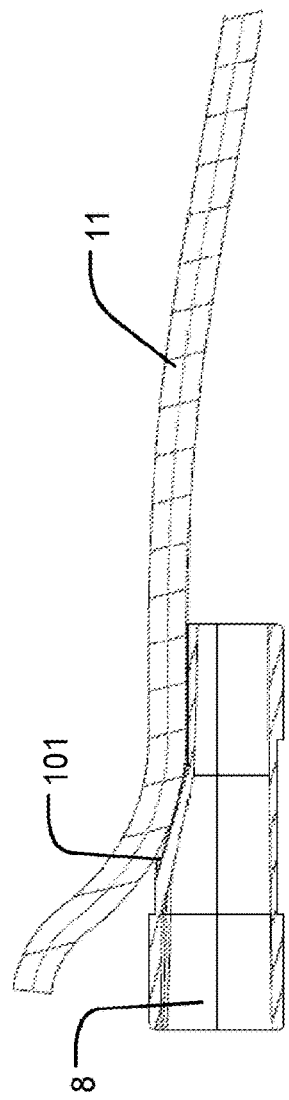

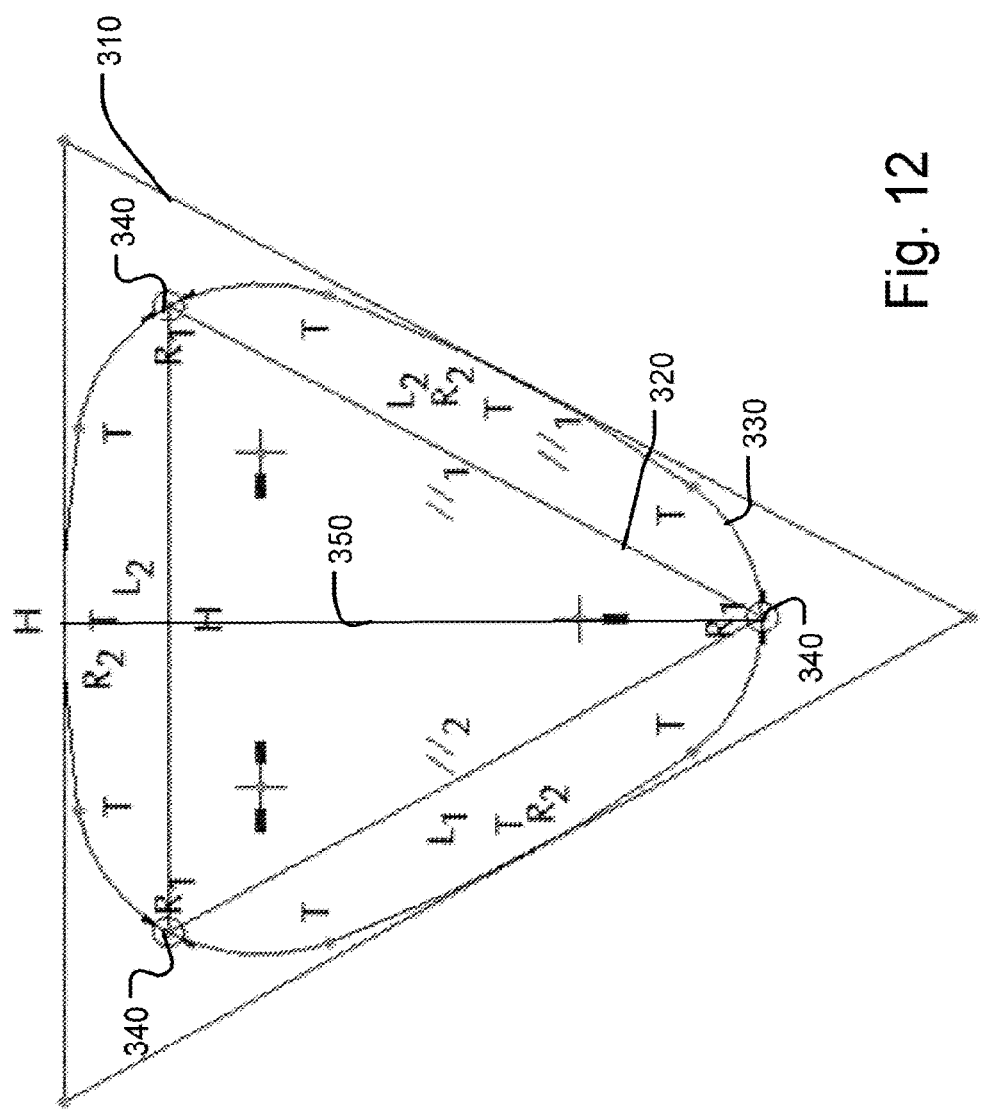

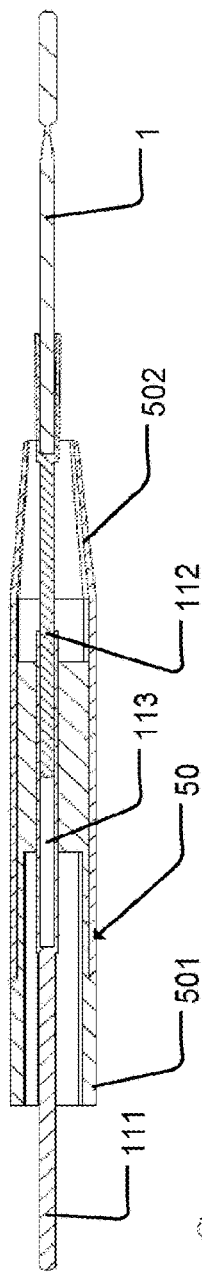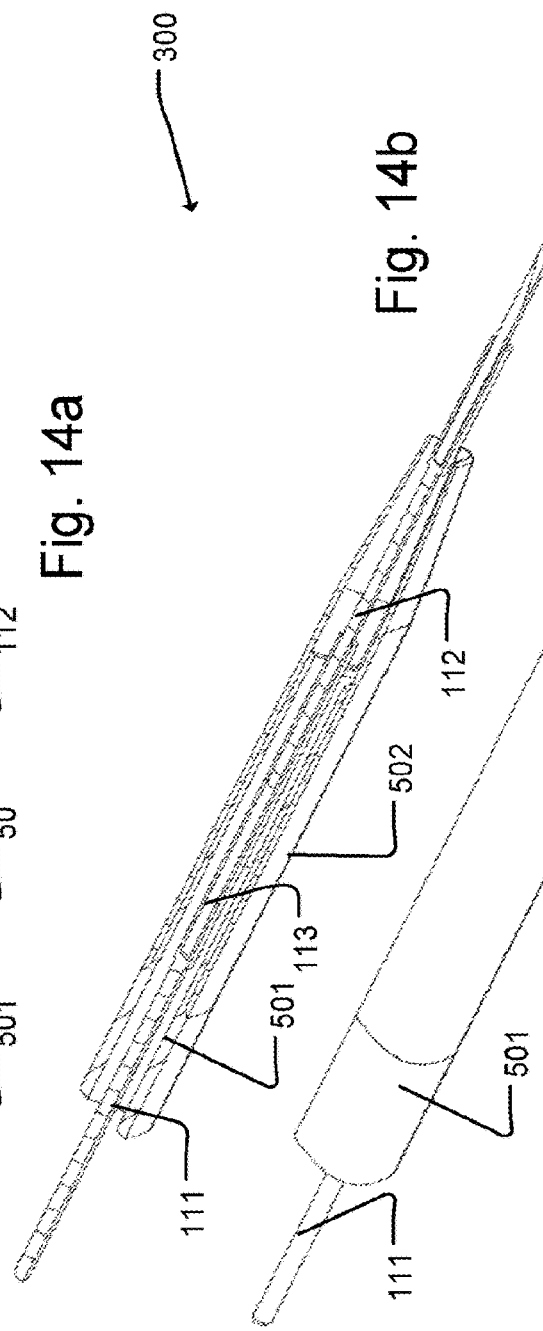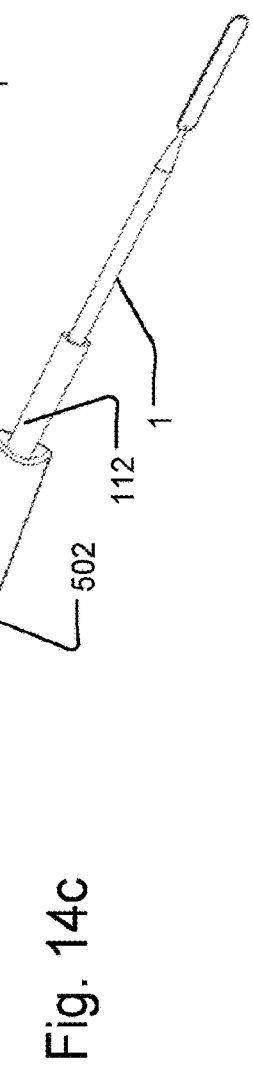
Fig. 14a
Fig. 14b
Fig. 14c

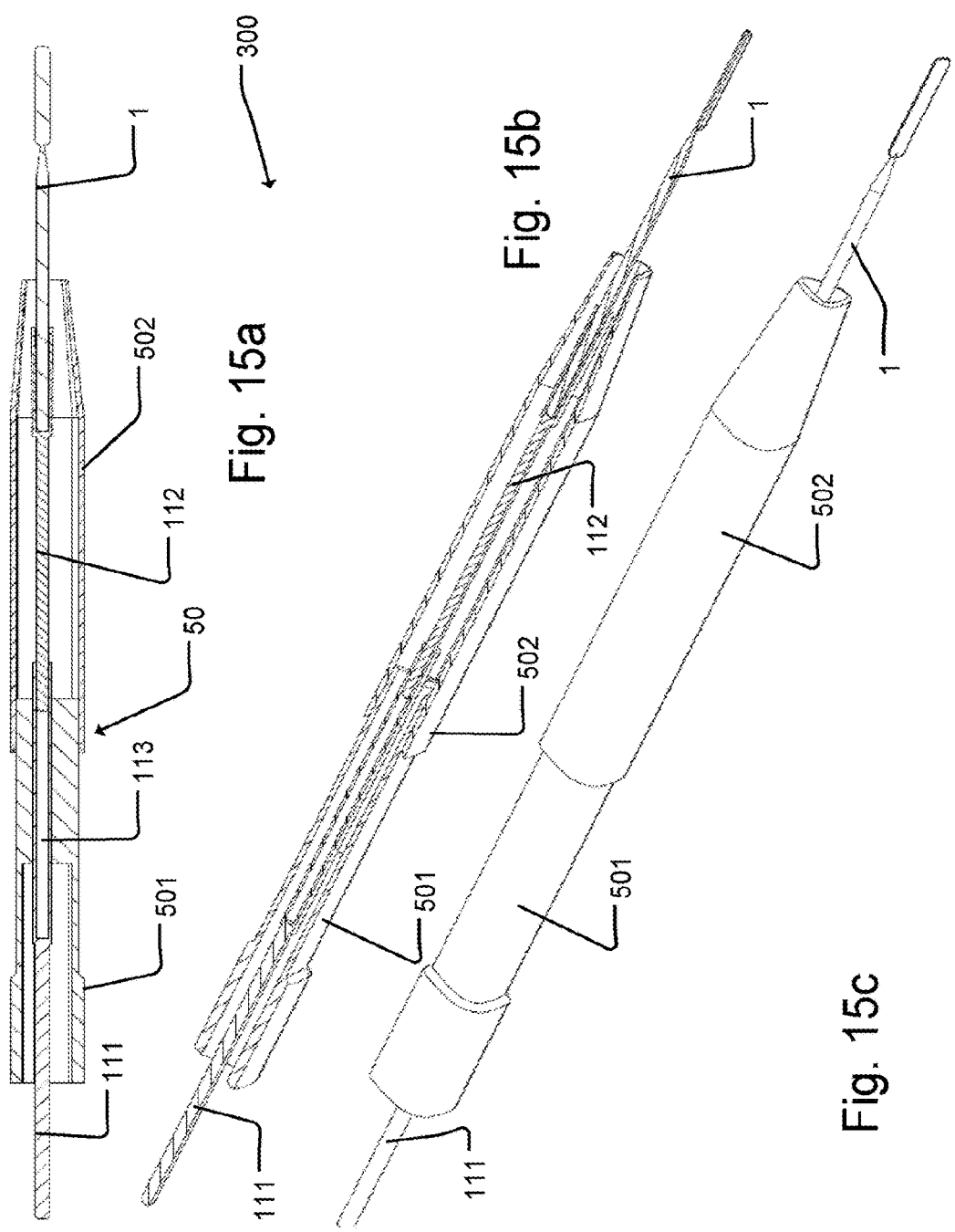

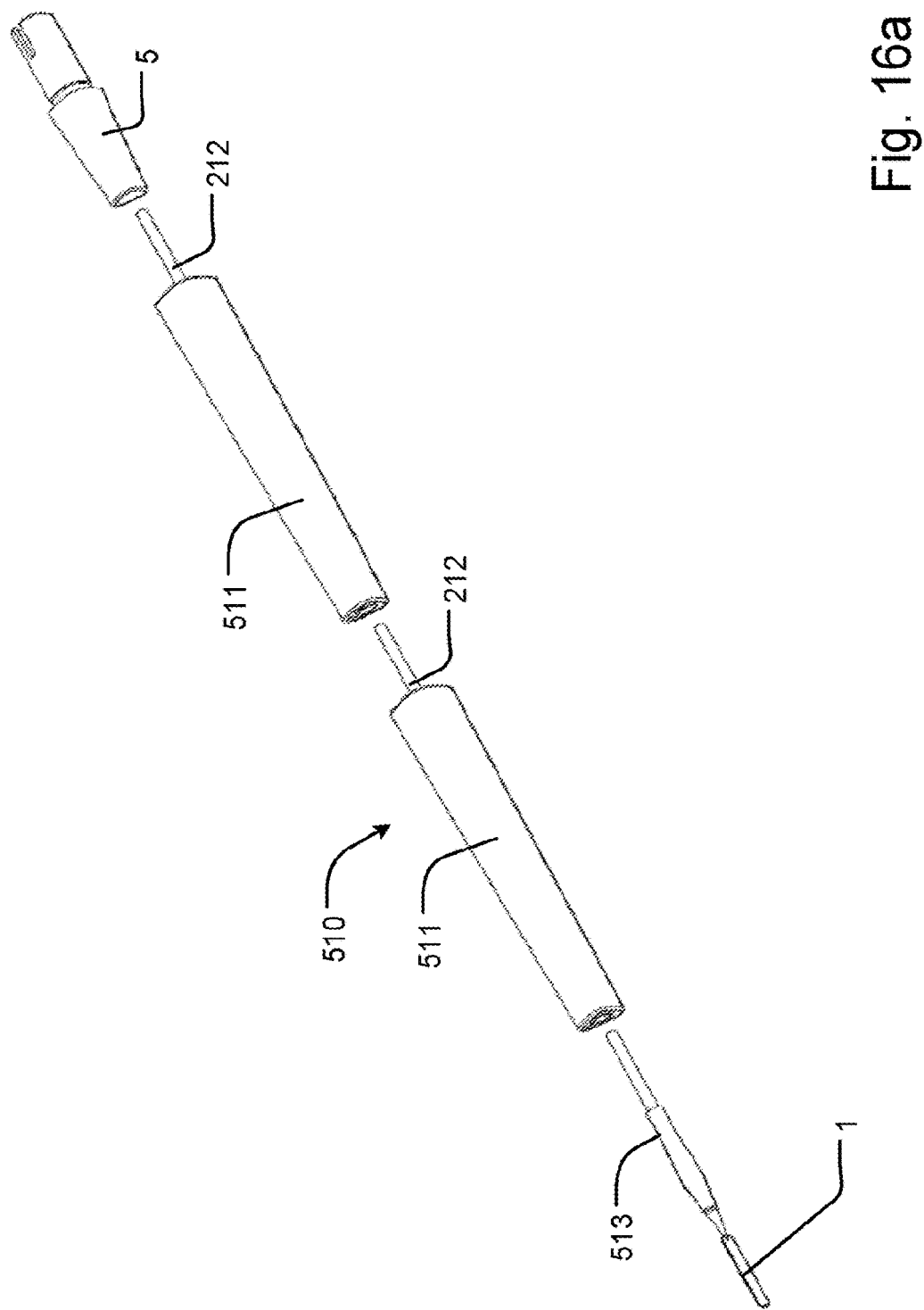

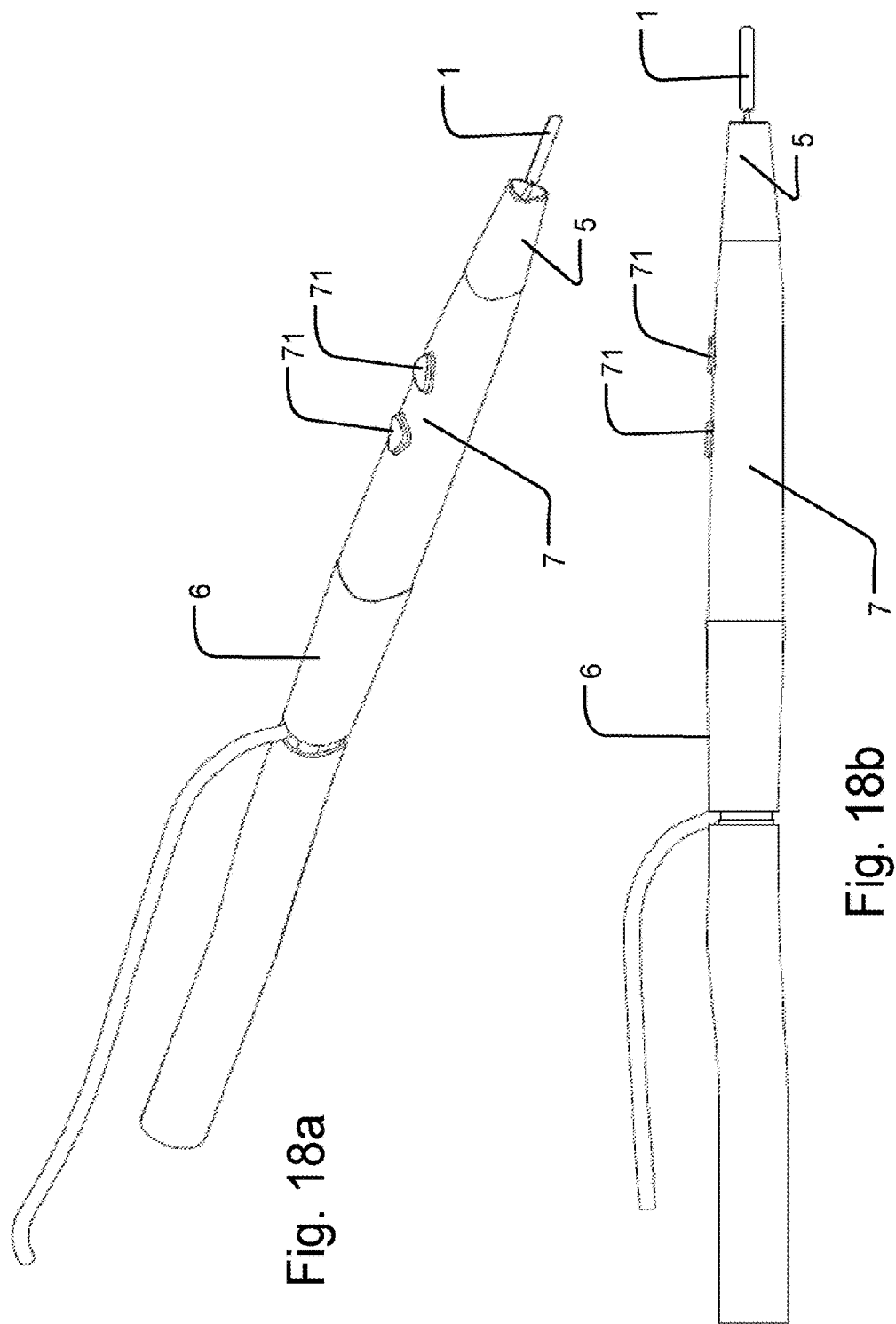

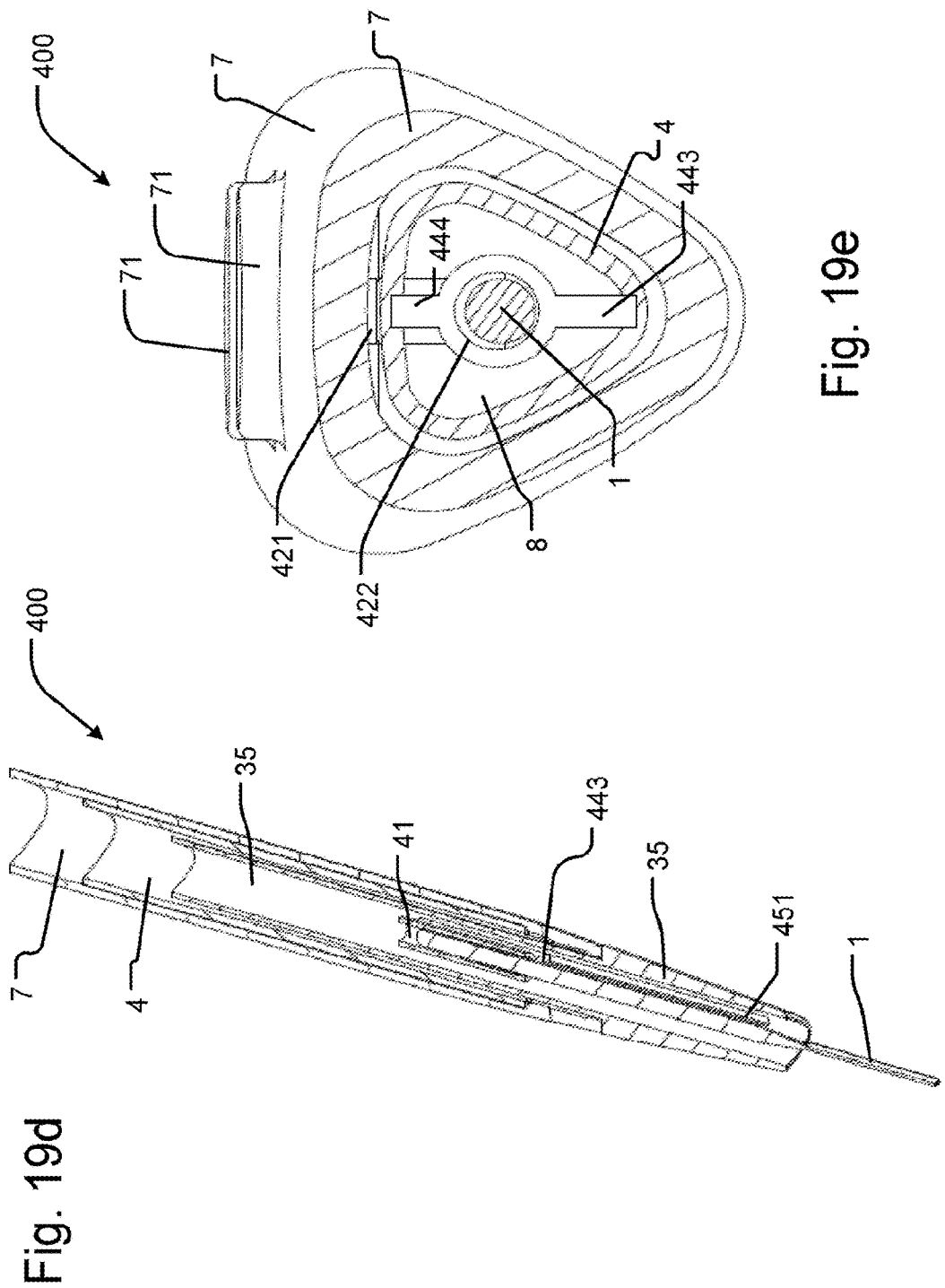

ELECTROSURGICAL PENCIL

CROSS REFERENCE TO RELATED APPLICATIONS

This application is a division of U.S. patent application Ser. No. 15/868,926 filed Jan. 11, 2018, which is a division of U.S. patent application Ser. No. 14/487,447 filed Sep. 16, 2014, now U.S. Pat. No. 9,901,391 B2, which is a division of U.S. patent application Ser. No. 14/114,476 filed Oct. 28, 2013, now U.S. Pat. No. 8,858,550 B2, which is a 371 filing of International patent application No. PCT/DK2012/050176 filed May 18, 2012, which claims priority to Danish patent application no. PA 2011 70251 filed May 19, 2011.

BACKGROUND

The invention relates to an electrosurgical pencil adapted to receive an electrode controllable by an electrical signal for performing surgical operations, comprising: a housing, a circuit, switching means adapted to be activated from outside the housing for closing the circuit, wherein the housing comprises receiving means (for receiving the electrode. The invention further relates to a kit of parts comprising an electrosurgical pencil and a method of providing an electrosurgical pencil and a kit of parts.

Electrosurgical pencils are used during operations for, for example, cutting in tissue or coagulating blood by delivering a high voltage, high- or radiofrequency current from a source of electricity to an electrode of the pencil. Depending on the waveform of the current, the pencil has a cutting or coagulating effect on the tissue. Some pencils are provided with means for evacuating smoke from the operation site as the smoke is known to contain viral DNA, bacteria, carcinogens and irritants.

Generally, electrosurgical pencils are constructed of two elongate housing parts assembled lengthwise, one of which is provided with hole for accommodating control buttons. The pencil is at the forward end provided with a bore, through which an electrode/blade projects. From the rearward end a cable extends from an aperture. The cable is connected to a printed circuit board inside the housing.

Such a pencil is known from US 2009/0062791. This pencil further comprises a switch module, comprising the printed circuit board upon which two dome switches are positioned. The buttons are located above the respective dome switches. A resilient sleeve encloses the printed circuit board and the dome switches inside the housing. The resilient sleeve acts as a gasket to prevent the escape of low pressure air from the interior of the housing at the buttons, and to prevent the smoke and other debris from contaminating the switches. A wire conducts a radio frequency electrosurgical waveform from the printed circuit board to an electrode anchor unit. The anchor unit comprises several conductive elements.

Another such pencil is known from U.S. Pat. No. 4,625,723. Here, a resilient strip of electrically conductive metal or alloy connects the electrode and the printed circuit board. Push buttons under which a dome member and a metal disc are provided, bridges contacts to the printed circuit board when the button is pushed.

Though pencils of this kind are widely used, they suffer from a number of disadvantages, among others the large number of different parts that are used complicate the production process and the many parts clutters the limited space available in the pencil so the space cannot be used to provide an effective suction channel. Additionally, the many parts make the device larger and not particularly comfortable to work with.

SUMMARY OF THE INVENTION

The invention now provides an electrosurgical pencil with improved energy transmission and a simple construction that eases the production process considerably. This is achieved with a flexible printed circuit, wherein the flexible circuit is positioned such that the flexible circuit is in direct contact with the electrode, when the electrode is positioned in the receiving means.

An electrosurgical pencil is provided which is adapted to receive an electrode controllable by an electrical signal for performing surgical operations, comprising: a housing, a circuit, switching means adapted to be activated from outside the housing for closing the circuit, wherein the housing comprises receiving means for receiving the electrode, If the circuit is a flexible circuit, the flexible circuit is positioned such that it is in direct contact with the electrode, when the electrode is positioned in the receiving means.

By positioning the circuit in direct contact with the electrode, a better contact between the electrode and flexible circuit is provided as no intermediate elements are required. Additionally, the construction is simpler and requires fewer steps in the production of the pencil. Usually, a metal bushing would be required, but now the receiving means can be provided in the same material as the main housing part where the receiving means may be located. Furthermore, the pencil is less cluttered on the inside and thereby opens up for the possibly of integrating a suction channel, while at the same time keeping the pencil slim and easy to handle. The advantage of the flexible circuit is that only one switch is activated when the flexible circuit is indirectly pressed. In case of a less flexible circuit, such as a printed circuit board, all switching means would be activated when the circuit is pressed, as the pressure would be distributed and hence applied to all the switches below the circuit.

The flexible circuit may further comprise a first portion and a second portion, wherein the second portion is substantially parallel with the first portion, when mounted in the housing. By bending the flexible circuit and making the two portions parallel in the mounted position, the complete flexible circuit does not have to be integrated in the receiving means and thereby the housing parts are easier to produce.

The housing comprises a sheath in a soft and resilient material, which sheath encloses mainly the main part of the housing and the sheath has actuators that are integral with and protrude from said sheath.

The switching means may comprise a switch and the actuator. Dividing the functionality between the switch and the actuator improves the flexibility of design and ease of manufacture even further. In preferred further developments of this embodiment, the first portion of the flexible circuit is positioned between the actuator and the switch, and the back of the switch is facing the actuator. By turning the switch so to speak upside down, the flexible circuit together with the actuator provides two layers of insulation without using an extra material layer. Additionally, this position of the switch gives a better response to the user and makes the actuator easy to press so that the switch is activated even if only the edge of the activator is pressed. Furthermore, a more resilient material may be used for the actuators.

The housing may comprise a sheath, wherein the thickness of the sheath is greater than 0.35 mm in the area of the switching means. The thickness provides a better protection in general and against tearing in particular.

At least a part of the second portion of the flexible circuit may be positioned between the electrode and the receiving means, when the electrode is positioned in the receiving means. This provides a better contact between the flexible printed circuit and the electrode, as the flexible printed circuit is shaped according to the form of the electrode and the receiving means and thereby provides a larger area of contact.

The receiving means may be a bushing. The bushing is a preferred receiving means and is easily formed in the main housing part. The bushing may be provided in various shapes, such as conical, pyramid shaped etc.

A tapered form of the bushing on its inner side makes it possible to use various sizes of electrodes and at the same time securing a large area of contact with the flexible circuit. This is i.a. advantageous when using electrodes of slightly varying transverse dimensions.

The electrosurgical pencil may further comprise a suction channel. The suction channel may be provided along the length in the interior of the pencil. This eliminates the need for any external suction devices as the smoke generated by using the electrosurgical pencil may be hazardous. By integrating the suction channel into the pencil the pencil is more comfortable to work with and provides a better view for the surgeon of the operation site.

In a preferred embodiment, the exterior of the electrosurgical pencil has a substantially triangular shape. By giving the pencil a substantially triangular shape a good grip and good ergonomics are provided. Additionally, the substantially triangular shape provides a better view of the operation site for the surgeon, as the "flat" sides of the triangle takes up less viewing space as compared to the rim of a cross-sectionally circular pencil. Additionally, when suction is provided in the pencil and a suction tube is mounted on the proximal end of the second housing part, the surgeon is less inclined to allow turning of the pencil in response to the torsional load exerted by the suction tube when handling the pencil. With the substantially triangular shape the surgeon will automatically hold the pencil in the most comfortable position, where he has access to the actuators. He will thereby not be inclined to allow the pencil to turn, as he would if it was circular.

The suction channel may have a substantially triangular shape. This shape makes the most use of the space available in the substantially triangular shape of the exterior of the pen. If a circular suction channel was provided the suction volume would be substantially decreased.

The substantially triangular shape may be defined by the area ratio between a first triangle which circumscribes the substantially triangular shape and a second triangle inscribed in the substantially triangular shape, which area ratio preferably is between 1:1 and 3:1. This ratio provides a shape that possesses sufficient properties as to optimum use of space and still lies comfortably in the hand.

A radius of curvature in at least one corner of the substantially triangular shape may be between 1 mm and 5 mm, preferably between 2 mm and 4 mm. By having rounded corners, provided by this radius of curvature, there are no sharp edges, while at the same time the triangular shape is still present.

The flexible circuit may comprise at least a partial gold coating for creating a contact between the electrode and the flexible circuit. By using gold, a better contact between the electrode and the flexible circuit is obtained and the gold does not corrode.

The electrosurgical pencil may comprise a main housing part, provided with at least one indentation adapted to receive a corresponding switch. One or more indentations may be provided in correspondence with the number of switches. By providing the housing with an indentation, the switch cannot shift and the switch or switches cannot be seen or felt as bumps on the outside of the housing.

The electrosurgical pencil may comprise a second housing part, provided with a guide recess for receiving a cable. The recess makes it easier to install the cable as it is easier to slide the cable into a recess ending in a hole than it is to simply put the cable through a hole without any guiding means. The recess additionally provides support for the cable when mounted.

A first housing part, attachable to a main housing part, may be provided wherein the first housing part may comprise a slit adapted to engage with the flexible circuit. The slit is both adapted to engage with the flexible circuit as well as with the first support member, keeping the flexible circuit in a correct position with respect to the main housing part.

Any of the first, second and main housing parts may be adapted to be assembled crosswise. By assembling the parts this way, the manufacture and assembly operations are facilitated.

In a second aspect of the invention, a kit of parts is provided. The kit comprises an electrosurgical pencil as defined, a tube, a cable, and a connector. This makes it possible to provide the parts necessary for carrying out the surgical operation or operations desired.

Preferably, the tube is attachable to a proximal end of the electrosurgical pencil, the cable is connected to the electrosurgical pencil and extends through the tube and the connector is attachable at the distal end of the tube, wherein the connector is provided with a cable recess for guiding the cable out of the tube. This provides for a secure and reliable design, which is furthermore easy to handle.

In a preferred development of this embodiment of the kit, a suction channel is provided in the tube and the cable is separated from the suction channel by a partition wall in the tube, which enhances the security and ease of operation even further.

According to third and fourth aspects of the invention, a method of assembling an electrosurgical pencil and a kit of parts, respectively, is provided.

The terms first, second and main housing parts do not indicate any specific configuration, order or position of the housing parts. The parts may be positioned in a different order, such that for example the main housing part is actually positioned at the most distal end of the pencil.

BRIEF DESCRIPTION OF THE DRAWINGS

In the following, the invention will be described in further detail with reference to the drawings, where FIGS. 7a-7b are perspective views of a second embodiment of an electrosurgical pencil according to the invention, FIGS. 9 and 9a-9b are vertical cross sectional lengthwise views, where the respective ends of the device have been magnified in FIGS. 9a-9b, FIGS. 10a-10d are different views of the connector, FIGS. 11a-11b are different views of the connector with a cable mounted, FIG. 12 is an example of the triangular shape of the pen, FIGS. 14a-14c show a second embodiment of the detail of the electrosurgical pencil of FIG. 13, where the electrode is in an extended position, FIGS. 15a-15c show a second embodiment of the detail of the electrosurgical pencil of FIG. 13 in another position, FIGS. 16a-16b shows a second embodiment of an extension device in a perspective view and a cross sectional view, respectively, FIGS. 18a-18b show the pencil as seen in FIG. 17 with a tube connected thereto, FIGS. 19a-19e show a third embodiment of the electrosurgical pencil in three different positions and two cross sectional views, respectively,

DETAILED DESCRIPTION OF THE INVENTION

Figure 8:
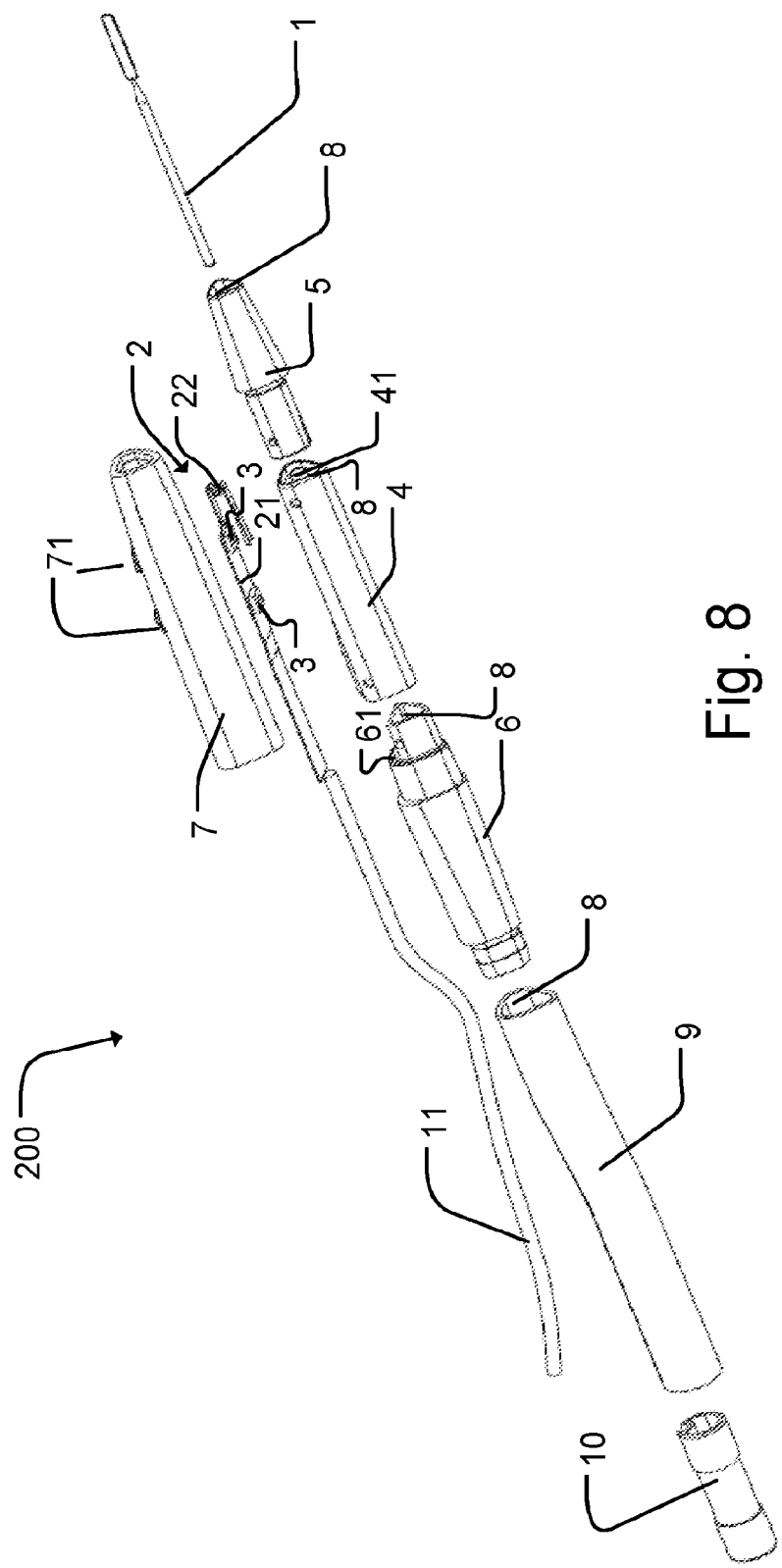
FIG. 8 is an exploded view an electrosurgical pencil according to the invention.
Figures 13A, 13B, 13C:
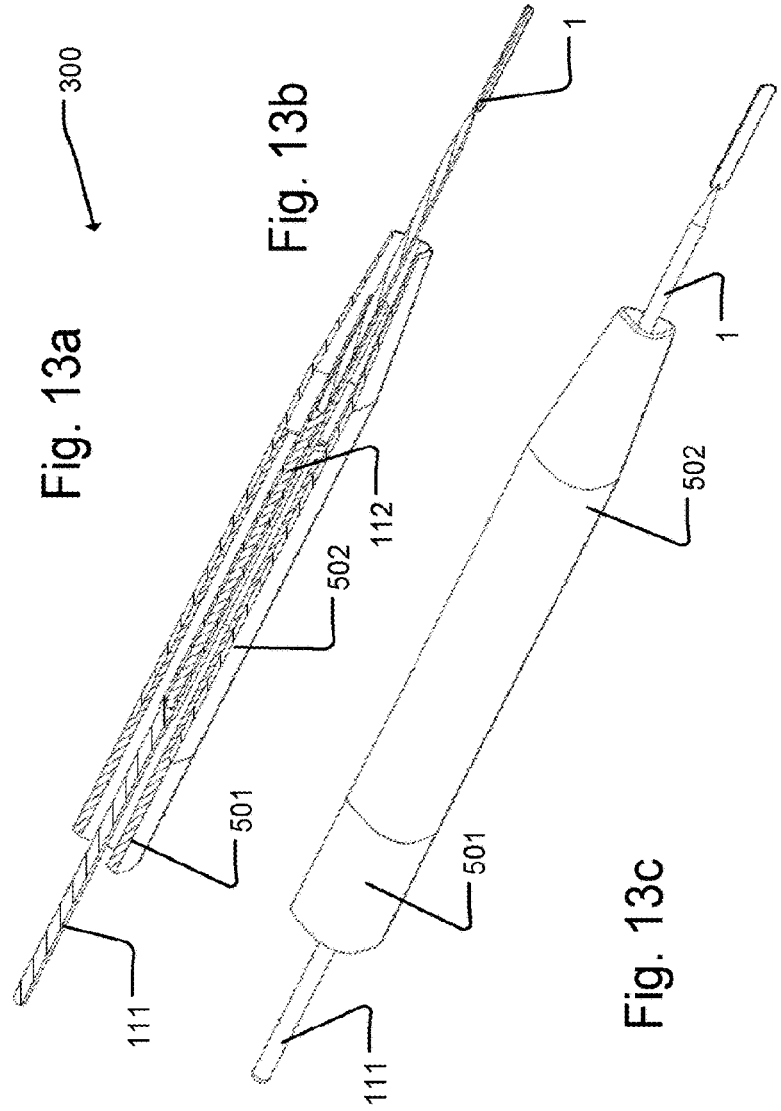
FIGS. 13a-13c show a second embodiment of a detail of an electrosurgical pencil according to the invention in a non-extended position.

FIGS. 1-6 represent a first embodiment and parts thereof. FIGS. 7-9 show a kit of parts where further features have been added to the first embodiment. FIGS. 10a-d and 11a-b show a connector which is a part of the kit of parts. FIG. 12 show an example of a substantially triangular shape and it shows how this is defined.

When referring to the respective ends of the different parts of the pencil and the kit of parts, the end closest to the opening for receiving the electrode is referred to as the distal end of each part, while the opposite end is referred to as the proximal end for each part.

One embodiment of a pencil according to the invention is shown in FIGS. 1-6. Here, the pencil 100 is in an assembled state, in which the individual parts and elements are mounted. As seen from the outside the pencil comprises two actuators 71, here in the form of buttons, but it may also be rocker buttons. In the embodiment shown, the pencil 100 further comprises a sheath 7 in a soft and or resilient material such as silicone or rubber. Additionally, the pencil 100 comprises a first housing part 5 and a second housing part 6. An electrode 1 is projecting from the first housing part 5. As will be described in further detail below, the pencil 100 has a substantially triangular shape with rounded corners. The housing parts are adapted to be assembled crosswise but may also be assembled lengthwise, or configured in any other manner.

The first embodiment of the invention will now be described with reference to FIGS. 2-5. In addition to the features discloses in FIG. 1 the pencil may additionally comprise an electrode 1.

The electrosurgical pencil 100 may be reusable and the electrode 1 disposable. The pencil may also be disposable. The disposable version may have an electrical cable embedded in a suction tube positioned at the end of the suction channel of the pencil. The reusable pencil may have the electrical cable attached to the end of the pencil however the cable may be positioned outside the suction tube.

The part of the electrode 1 adapted to be mounted in the receiving means 41 is between 2.2 and 2.6 mm in diameter. The overall cross-sectional dimensions of the electrode may be between 1-3 mm in diameter. The electrode 1 is adapted to be mounted in a bushing or other receiving means 41 of the main housing part 4.

The electrode may be selected from the group consisting of a blade electrode, a needle electrode, a ball electrode, a conization electrode, a loop T-bar electrode, an arthroscopic electrode, an electrode extender, all of them with or without non-stick coating. This ensures that the pencil can be used for a variety of purposes.

In the embodiment shown, the housing generally designated 4,5,6,7 comprises the first, second and main housing part 4,5,6 and the sheath 7. The electrosurgical pencil may consist of a housing, a flexible circuit, an electrode receiving means and a switch, wherein the pencil is adapted to be connected to a cable and an electrode.

The housing parts 4,5,6 and parts of the kit of parts, including tube 9 and a connector 10, are made from any suitable material or polymer, such as ABS, PSU, high density polymer (HDPE) or low density polymer (LDPE), or polyvinylchloride (PVC). The housing is free from phthalates, but may also be made in a phthalate containing material.

The transverse dimension 350 of the housing 4,5,6,7 is around 14.5 mm measured from a corner of the substantially triangular shape, to the opposing side, at the widest point. The overall dimension of the housing 4,5,6,7 may be slightly larger, such as less than 16 mm, or less than 14.5 mm, such as 12 mm, measured from a corner of the substantially triangular shape, to the opposing side, at the widest point.

The length of the pencil 100 is less than 15.5 cm. The pencil may also be longer such as less than 20 cm, or less than 17 cm.

The weight of the pencil 100 is 14 g. The pencil 100 may be heavier and weigh less than 16 g, or less than 18 g.

The housing 4,5,6,7 may be formed in one piece or the second housing part 6 and main housing part 4 may be formed in one piece, or the first housing part 5 and the main housing part 4 may be formed in one piece. The first housing part 5 is adapted to slide into the main housing part 4 forming a fluid tight seal between the two.

The second housing part 6 is adapted to slide into the main housing part 4 forming a fluid tight seal between the two. The second housing part 6 is further provided with a compartment 61 adapted to accommodate the end of the first portion 21 of the flexible circuit 2. The compartment 61 is separated from the suction channel 8.

The second housing part 6 is additionally provided with a guide recess 62 for receiving an electric cable. At the bottom of the recess the second housing part 6 is provided with an aperture, such that the cable can be connected with the flexible circuit 2 inside the housing. The first portion of the flexible circuit 21 extends into the second housing part 6 from the main housing part 4. The space 61 for the cable inside the second housing part and for the flexible circuit 2 is separated from the suction channel 8.

The first housing part 5 is hollow and tapered at the distal end and has an aperture from which the electrode projects. The first housing part 5 is triangular in shape and has rounded corners. The triangular shape makes the tip of the pen comfortable to hold, which is particularly useful when doing child surgery or other fine surgery that require a large degree of precision. In this case the surgeon will often hold the distal end of the pen. The pencil may be controlled via a foot pedal instead of via the actuators, as a more steady hand may be required. It may also be other shapes such as circular or have sharp corners. It is further provided with a first slit 51 and a second slit 52 at the proximal end. The slits are positioned directly opposite each other. The slits 51, 52 may be positioned elsewhere along the edge of the first housing part.

The first and the second housing parts are provided with notches 55, 65, which, in an assembled state, define a shore area there between, where the sheath 7 is positioned.

The main housing part 4 has a triangular shape with rounded corners. It may also be other shapes such as circular or have sharp corners. The main housing part 4 comprises receiving means 41, in form of a bushing, which is tapered. The receiving means 41 may be straight, conical, pyramid shaped or polygon shaped or be circular at the opening of the receiving means and polygon shaped at the bottom of the receiving means 41 or vice versa. The top of the aperture of the receiving means 41 where the flexible circuit enters the receiving means is rounded, meaning that in a cross section of the pencil an exterior circumference of the receiving means is circular. The flexible circuit is thereby curved cross-wise in the point where it is folded, and enters the receiving means. In a cross-section of the pencil an exterior circumference of the receiving means may be flat on the top, however keeping its shape of the interior circumference. A wedge segment may have been removed from the top of the opening of the receiving means. This removes the stress on the flexible circuit, that in this specific point is bent around 180 degrees and by flattening the top of the opening, the flexible circuit is only bent in one plane instead of two, as a circular exterior circumference of the receiving means requires the flexible circuit to adapt to the curved shape of the receiving means.

The receiving means 41 is positioned in the center at the distal end of the main housing part 4 facing the first housing part 5. The receiving means 41 may also be in the form of a number of rings for supporting the electrode 1 or a number of bars or rods running in parallel to the electrode 1. The receiving means is made of plastic and/or is cast in one with the main housing part 4.

A first support member 44 is provided at the distal end inside the main housing part 4. The first support member 44 is retracted from the edge of the distal end of the main housing part 4. It functions both as a support for the receiving means 41 and it functions as a stopper for the first housing part 5 when this is slid into an assembled position. When assembled, the crease of the flexible circuit 23 is positioned between the support member 44 and the edge of the first housing part 5. A first slit 51 in the first housing part is adapted to engage with the flexible circuit 2 as well as with the first support member 44. The second portion of the flexible circuit 22 is adapted to engage with the first housing part 5 and is therefore narrower than the first portion of the flexible circuit 21, as the second portion is adapted to enter the receiving means and have to adapt to the shape electrode.

A second support member 43 is provided opposite the first support member 44. When assembled the second support member 43 engages with the second slit 52. The second support member also provides support for the receiving means 41.

One or more indentations 42 are provided along the length of the main housing part 4. These indentations 42 are used to accommodate the switches 3 in order to keep the pencil slim.

The interior of the main housing part 4 surrounding the receiving means 41 forms a suction channel 8, which extends through the first housing part 5, main housing part 4 and the second housing part 6. The suction channel 8 is used to evacuate smoke and aerosols and particles from the surgical site. The suction channel 8 within the housing parts 4, 5, 6 has in the embodiment shown a substantially triangular shape 330. The suction channel may also have other shapes, such as a circular shape.

The flexible circuit 2 comprises a first portion 21 and a second portion 22 and a middle crease 23. In the embodiment shown, the first portion of the flexible circuit is 67 mm long, 7.5 mm wide and around 0.14 mm thick. This corresponds to a volume of approximately 70 mm$^3$. The second portion is about 37 mm long and 2 mm wide and 0.14 mm thick. The second portion is cut out of the first portion of the flexible circuit and does therefore not add to the volume. By cutting the second portion out of the first portion of the flexible circuit a smaller, and square shaped, circuit may be produced and less waste may be generated during production. The second portion of the flexible circuit may be other sizes and it may be produced separately from the first portion. The first portion comprises the control structure while the second portion 22 is adapted to connect with the electrode 1 in the bushing 41. The flexible circuit 2 is of a paper thin flexible material, such as a foil, with a control structure printed upon it. When mounted the flexible circuit 2 is folded as shown on the figure with three creases. When assembled the first crease abuts against the edge of the receiving means 41, the middle crease 23 abuts against the bottom of the first slit 53 of the first housing part 5 and the second crease abuts against the edge 46 of the main housing part 4. The flexible circuit 2 may be arranged in other ways, such that there for example is only one crease. The flexible circuit may also be folded more times or it may not be folded at all.

The flexible circuit may be selected from the group consisting of a flexible circuit board, a flexible printed circuit and flexible printed circuit board.

Figure 4:
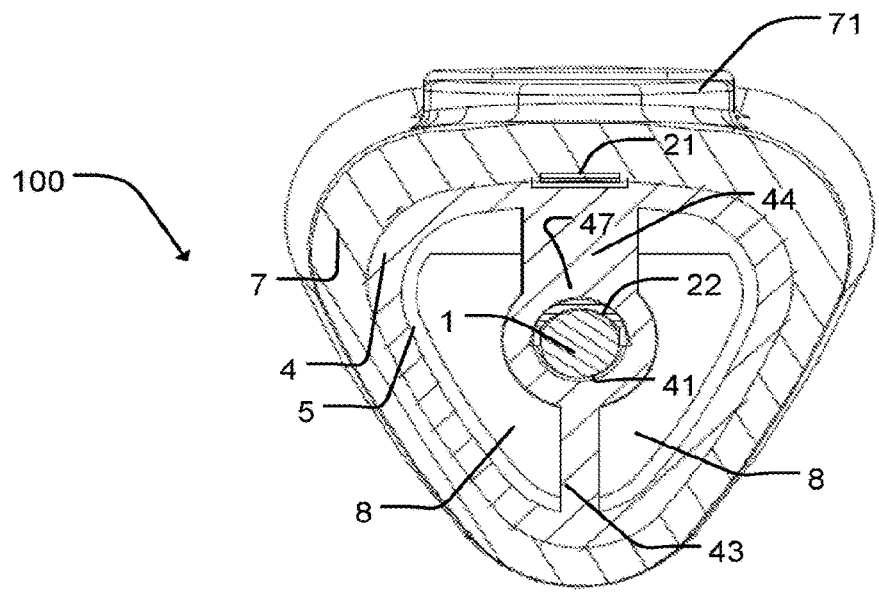
FIG. 4 is a cross sectional crosswise view.
Figure 5:
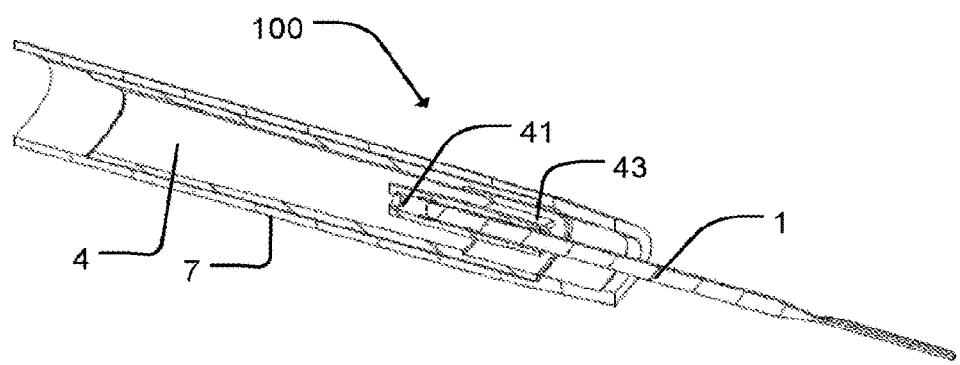
FIG. 5 is a horizontal cross sectional lengthwise view.
Figure 6:
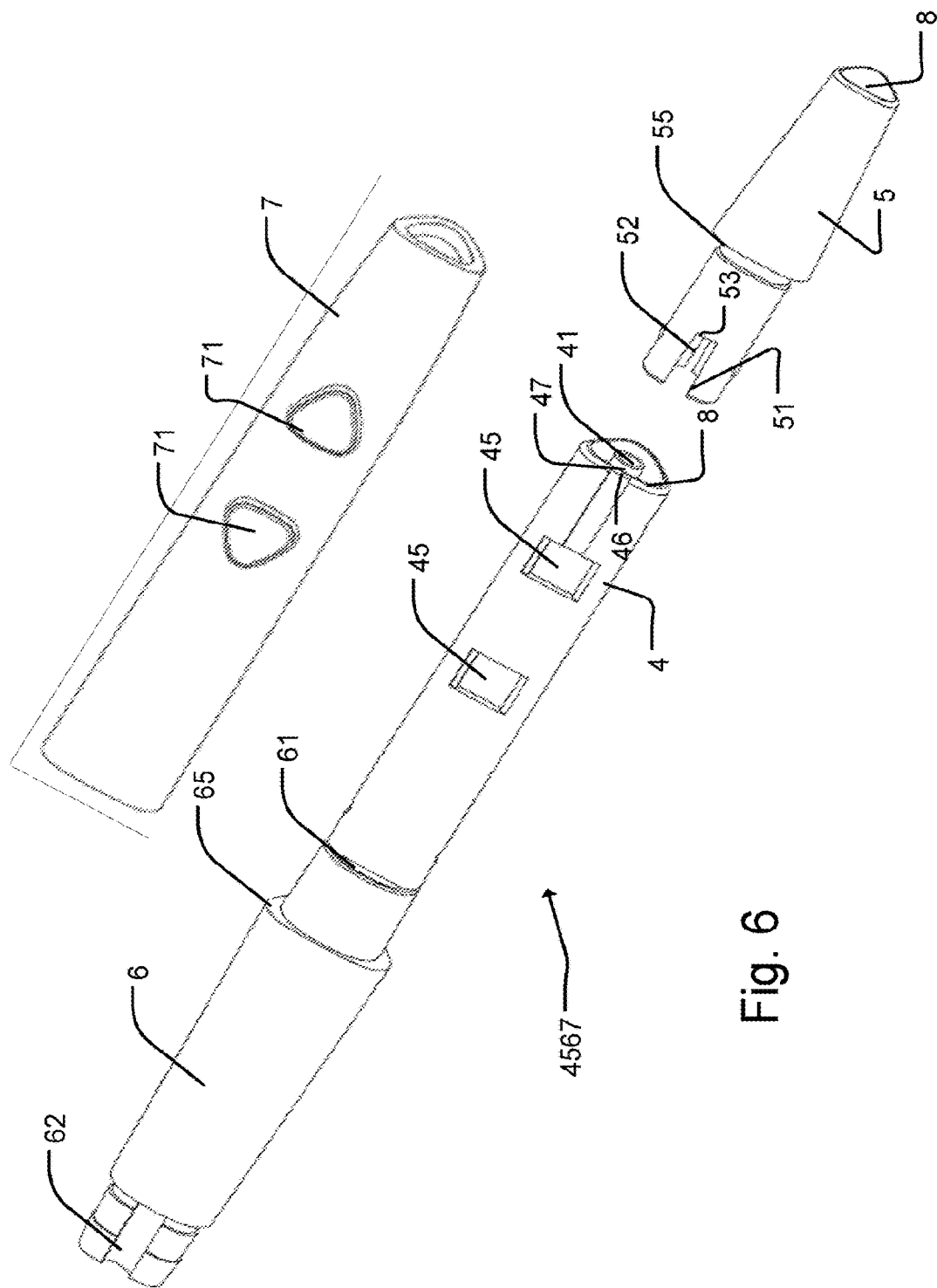
FIG. 6 is a perspective view of parts of the housing.

The second portion 22 is substantially parallel to the first portion 21, when mounted in the receiving means 41 of the housing 4,5,6,7. This is achieved by folding the flexible circuit 2 approximately 180 degrees. However, in the mounted position when the second portion of the flexible circuit is in the receiving means, the angle is slightly less than 180 degrees, which can be seen from FIG. 8. But the two portions 21, 22 are still even in this position, substantially parallel. Several foldings may be used to achieve the same effect. The first portion of the flexible circuit may be positioned between the actuator 71 or button and the switch 3. The flexible circuit is provided with a gold coating, on a part of the second portion 22 of the flexible circuit 2. It may also be provided with another conducting coating such as silver, copper or tin. The flexible circuit is to a great extent covered by a film, such that the conducting parts are not exposed. However, on the second portion of the flexible circuit 22, this foil is not present, at least on one side, and the conducting part of the circuit is therefore be in direct contact with the electrode 1, when the electrode 1 is in the receiving means 41. At least a part of the second portion of the flexible circuit 22 is to be positioned between the electrode 1 and the receiving means 41, when the electrode 1 is positioned in the receiving means 41. In FIG. 4 it can be seen how the second portion 22 of the flexible circuit is shaped according to the shape of the electrode 1, such that an optimal contact is obtained between the second portion of the flexible circuit 22 and the electrode.

A sheath 7 made of a resilient material, such as silicone or rubber, encloses mainly the middle part 4. It isolates the flexible circuit, which is the only conducting part connecting the electrode with the cable, from the user. Additionally, it provides the actuators/buttons 71 from where the user can control the activation of cutting and coagulating power from the generator. The suction may be controlled via these buttons as well. The sheath 7 is adapted to snugly fit the main housing part 4 with the flexible circuit 2 and the switches 3 in position for use. The thickness of the sheath 7 is greater than 0.35 mm in the area covering the switch 3. The sheath 7 may be expended with and instead a non-resilient housing part may used. This part may in turn be provided with apertures in which buttons may be positioned for activating the pencil.

The pencil further comprises two micro switches 3. The switches 3 form part of the switching means. Other switches that may be used include a dome, a metal dome switch, a metal tactile switch, a membrane switch or a membrane keypad. The switches 3 are attached to the flexible circuit 2. The switches 3 are positioned between the flexible circuit 2 and the main housing part 4. The switches 3 are positioned upside down such that when the user presses the button, he actually pushes on the back of the switch. This is possible because the flexible circuit is so thin that the flexible circuit 2 flexes and thereby does not simultaneously activate both switches. If a non-flexible circuit had been used, the pressure on the button would have activated both switches. The flexible circuit 2 thereby makes it possible to activate the switch from the back side. It is thereby the resistance of main housing part that activates the switch. In this way there is no exposed circuit facing towards the activator 71. Thereby two layers of insulation from the circuit are provided in the form of the sheath 7 including the activators 71 and the flexible circuit 2, which does not have any conducting parts on the face facing the sheath 7. The volume of the flexible circuit 2 and the switches 3 is minimal and takes up less than 0.15 cm$^3$ of space. The volume of one switch is less than 35 mm$^3$. The conducting part and the switch may be sized such that the volume of the two parts is less than 0.5 cm$^3$ or less than 0.3 cm$^3$. The switch may be less than 60 mm$^3$, or less than 40 mm$^3$. This small volume maximizes the space for a possible suction channel within the housing.

This means that the volume of an optional suction channel 8 is optimized as the only remaining parts are the housing and the means for supporting and receiving the electrode.

When using a flexible circuit 2 and micro switches 3 or small switches in general, the electrode 1 may extend beyond the most distal switch 3, such that the distance from the tip of the electrode to the actuator positioned on top of the switch is minimized. When doing surgery, the actuators will be close to where the surgeon's fingers are positioned and thereby he will not have to rearrange the pen in his hand to reach the actuators.

When one of the buttons 71 is pressed down, the first portion of the flexible circuit 21 is adapted to flex and the switch 3 is pressed against the indentation 42 in the main housing part 4. A signal is sent to the control structure on the flexible circuit 2 and the electrode 1 is activated. When the button 71 is pushed down the user may hear a clicking sound or feel a tactile feedback such that the user is aware that the pencil has been activated.

When the pencil 100 is in use, it is connected to a generator (not shown), by a cable 11. The patient is provided with a grounding plate somewhere on the body. The electrode thereby forms one pole and the patient forms the other. The generator to which the pencil is connected to delivers power with a frequency of minimum 350 kHz.

Figure 17:
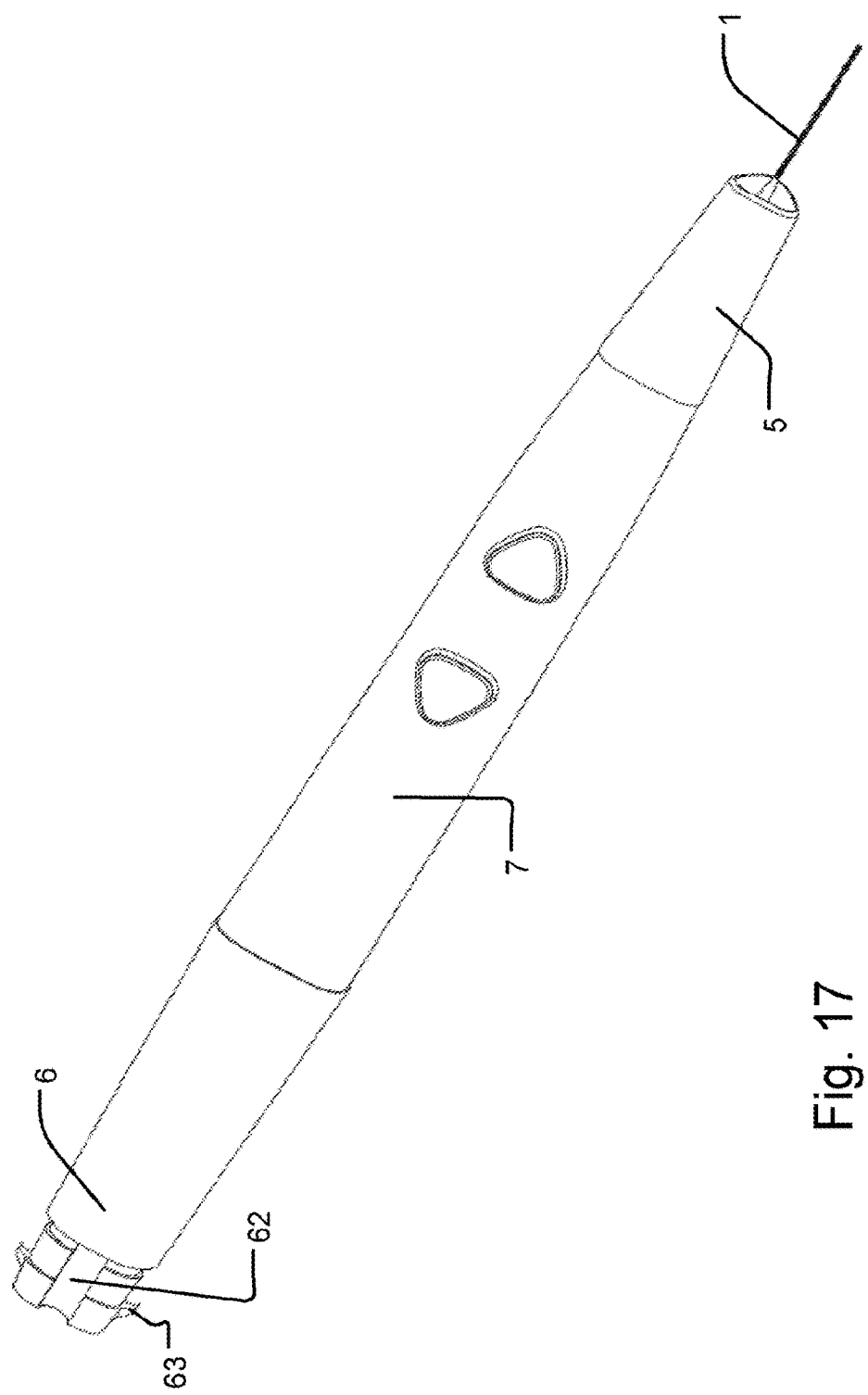
FIG. 17 shows the pencil with a second embodiment of the second housing part 6.

The kit of parts in FIGS. 7-9 comprises an electrosurgical pencil 100, a tube 9, a cable 11 and a connector 10. The kit may comprise any other features as disclosed in the first embodiment. Each of the features is independent of each other unless explicitly stated so, and may therefore be added to the kit independently of each other. The tube 9 is adapted to be mounted on the second housing part 6 at the proximal end. The second housing part 6 is provided with one or more projections for retaining the tube 9, such the tube 9 can be securely mounted. The tube 9 is made in a plastic material. The tube 9 may function as a suction channel for guiding smoke, aerosols and particles to a container for collection. The tube is therefore connected to the suction channel 8. The tube 9 may furthermore be used for guiding the cable such that it does not get in the way when the surgeon works. At the proximal end of the tube 9 a connector 10 may be mounted. The connector 10, such as a splicing sleeve, is made in a polymer material. It is provided with a cable recess 101 such as the one provided in the second housing part 6, and is used for guiding the cable 11 to the exterior of tube 9. A seal that is sufficiently tight such that no particles can escape is provided between the cable 11 and the connector 10. The cable is provided within the suction channel. The cable 11 may be separated from the suction channel in the tube 9 by a partition wall. Such a separation provides the possibly to makes the electronic pencil reusable, along with further features. The connector 10 may be provided with barbs 63 as seen in FIG. 17. Further views of the connector 10 is shown in FIG. 10a-d and with a cable mounted, in FIGS. 11a-b.

FIG. 12 shows an example of the substantially triangular shape. The substantially triangular shape has the advantages that it is easier for the surgeon to see the tip of the electrode during surgery, as a circular shaped housing would be blocking some of the view that the substantially triangular shape exposes instead. The rounded corners of the triangle are defined by the radius of curvature R1. The radius of curvature is 2 mm at the distal end of the first housing part 5 and around 4 mm at the proximal end of the second housing part 6 at the widest point. The radius of curvature may vary locally. The sides of the substantially triangular shape are also defined by a radius of curvature R2. This is 8 times larger than R1 in any cross section of the pencil and provides a less curved line. It may also be from 3 to 10 times larger or merely a straight line. The substantially triangular shape 330 cuts through the corners 340 of the second equilateral triangle 320. The triangles 310, 320 are positioned with the second equilateral triangle 320 within the first equilateral triangle 310 such that their sides are parallel.

In the embodiment shown, the substantially triangular shape is defined by the area ratio between a first triangle 310 which circumscribes the substantially triangular shape and the second triangle 320 inscribed in said substantially triangular shape, is between 1:1 and 3:1. A ratio approaching 1:1 means that the substantially triangular shape is in fact virtually triangular including straight lines between the respective corners of the triangle. In the other end of the interval, the ratio 3:1 provides for a satisfying grip due to the curved outline. In the embodiment shown, the ratio is approximately 2.34.

The substantially triangular shape may be seen in only some or parts of the housing parts, such as the first, second and main housing parts, where the remaining parts may have a substantially circular shape. The distal end of the first housing part 5 may have a substantially triangular shape, while the proximal end of the first housing part 5 may have a substantially circular shape or vice versa. The housing may have any other cross-sectional shape.

In FIGS. 13a-c, 14a-c, and 15a-c, an embodiment of an extension device is shown. Each of the FIGS. 13-15 shows a lengthwise cross sectional view, a, a lengthwise cross sectional perspective view, b, and a perspective view, c, in three different positions of extension.

The extension device 300 comprises an extender 50. It is usable for either extending the suction channel and/or extending the electrode. The extender 50 is adapted to be positioned on the first housing part in the first embodiment. The first electrode extender is provided with a receiving means for the second electrode extender 112. The receiving means may be in the form of a bushing.

The extender 50 comprises a first extender part 501 and a second extender part 502. The first extender part 501 is adapted to slide in the second extender part 502. The second extender is tapered at the distal end. The second embodiment further comprises a first electrode extender 111 and a second electrode extender 112. The second electrode extender 112 is adapted to slide in the first electrode extender 111. The electrode 1 is positioned in the second electrode extender 112, but may be separate there from. The first and second electrode extenders are made of a conducting material. The first electrode extender 111 is adapted to be positioned in the receiving means 41 in the first embodiment. The second electrode extender 112 may project from the opening in the second extender part 502 when in the most retracted position.

In order to keep the second extender 502 and/or the second electrode extender 112 in the selected position, the fit of the first extender 501 and the first electrode extender may be sufficiently tight such that their respective positions are kept during an operation.

The second extender 502 and the second electrode extender 112 may be positioned in any position between the most retracted and most extended position. They may keep this position during an operation or the surgeon may adjust the position of the respective parts during the operation.

In FIG. 13 both the extender 50 and the electrode extender parts 111, 112 are in a non-extended position, such that the second extender 502 and the second electrode extender 112 are retracted as far back as possible and provides the shortest possible extender 50 and electrode extender parts 111, 112.

In FIG. 14 the extension device 300 is in an extended state. Here the second electrode extender 112 is positioned in its most extended position. The extension of the electrode may be used for reaching hard to reach places in the body, where the suction channel or second extender part 502 are not serving a purpose or are getting in the way, respectively.

In FIG. 15 the second electrode extender 112 and the second extender 502 are positioned in their most extended position. Here, if an extra long pencil and suction are required, this position serves both purposes.

The extension and retraction of the respective parts are performed by pulling and pushing the second parts 112 and 502, respectively.

Any parts of the second embodiment 300 may be combined with any parts of the first embodiment 100. In particularly the extension device 300 may be positioned as an extension on the first housing part 5. The first electrode extender 111 may be positioned in the receiving means 41, thereby creating an electrosurgical pencil with a telescopic suction channel and a telescopic electrode.

Figure 16B:
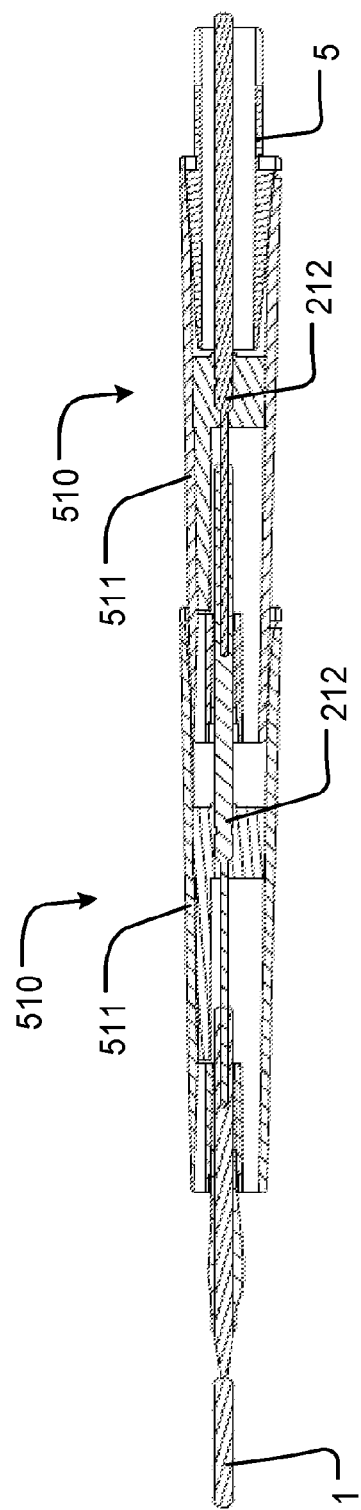

FIGS. 16a-b show a second embodiment of an extension device in a perspective view and a cross sectional view, respectively. Here an electrode extender 212 is comprised in a separate extension piece 510. The extension piece 510 comprises a pipe piece 511 and an electrode extender 212.

The pipe piece 511 is made of a transparent material, such that it is easier for the surgeon to see, what he is working with, as the pipe piece 511 doesn't block his view. The pipe piece 511 is made from plastic or other material that will not show on an X-ray picture. However, the electrode extender 212, which is made of a conducting material, such as metal, and which extends through the length of the pipe piece 511, will show on an X-ray picture, in case the extension piece 510 should be lost in a patient. Additionally, or alternatively, the pipe piece 511 may be made of other materials for example a polymer comprising barium sulfate. The barium sulfate makes the pipe piece 511 visible on an x-ray picture.

The extension piece 510 is adapted to be attached to an electrosurgical pencil of any of the other embodiments. The pipe piece 511 is adapted to be attached to the first housing part 5 and the electrode extender 212, which is provided inside the pipe piece 511, is adapted to be positioned in the receiving means 41 of the pencil as seen on the preceding embodiments. When the extension piece 510 is pushed onto the pencil, the electrode extender 212 is connected to the flexible circuit and a stable electronic connection is created. At the distal end of the electrode extender 212, the electrode may be positioned. Because an electrode extender 212 is used, there is no need to used different lengths of electrodes, and the surgeon may therefore use the same electrode no matter the required length of the pencil.

Additionally, the extension piece 510 is adapted to be positioned on another extension piece 510, making the pencil even longer, which is particularly useful when operating on larger patients. The extension piece 510 thereby fits onto itself. So instead of having to store different lengths of extender pieces, only one kind of extension piece is needed for providing different lengths. When a second extension piece 510 is attached to first extension piece 510, the electrode extender 212 of the first extension piece is pushed to a side such that the overlapping lengths of each electrode extender merely abut each other. Alternatively, each end of the electrode extender 212 may be formed as a plug and a socket, as seen in FIG. 13.

The electrode 1 is further provided with an insulation sheath 513, for holding on to the electrode 1 when inserting or removing electrode 1 from the pencil. The insulation sheath 513 may be dispensed with.

FIG. 17 shows a second embodiment of the second housing part 6. The second housing part 6 has here been provided with barbs 63. One or more barbs 63 may be provided. This is to ensure that the tube (not shown) conveying the material sucked from the patient's body is properly fixed. The tube is simply pushed over the barbs and as the material of the tube is slightly expanded where the barbs are positioned inside the tube, the tube stays fixed, but may be removed from the pencil by pulling the tube. The tube is, as in the previous embodiments, able to rotate around its axis. The tube may also be fixed such that it is unable to rotate. The cable providing the pencil with power may be positioned inside or outside the tube.

FIGS. 18a-b show the embodiment in FIG. 17 with a tube mounted directly on the pencil. Because the second housing part 6 is provided with barbs as seen in FIG. 17, it is possible to mount the tube directly on the pencil and the connector, as seen in FIGS. 8-10, can be dispensed with.

Figure 1:
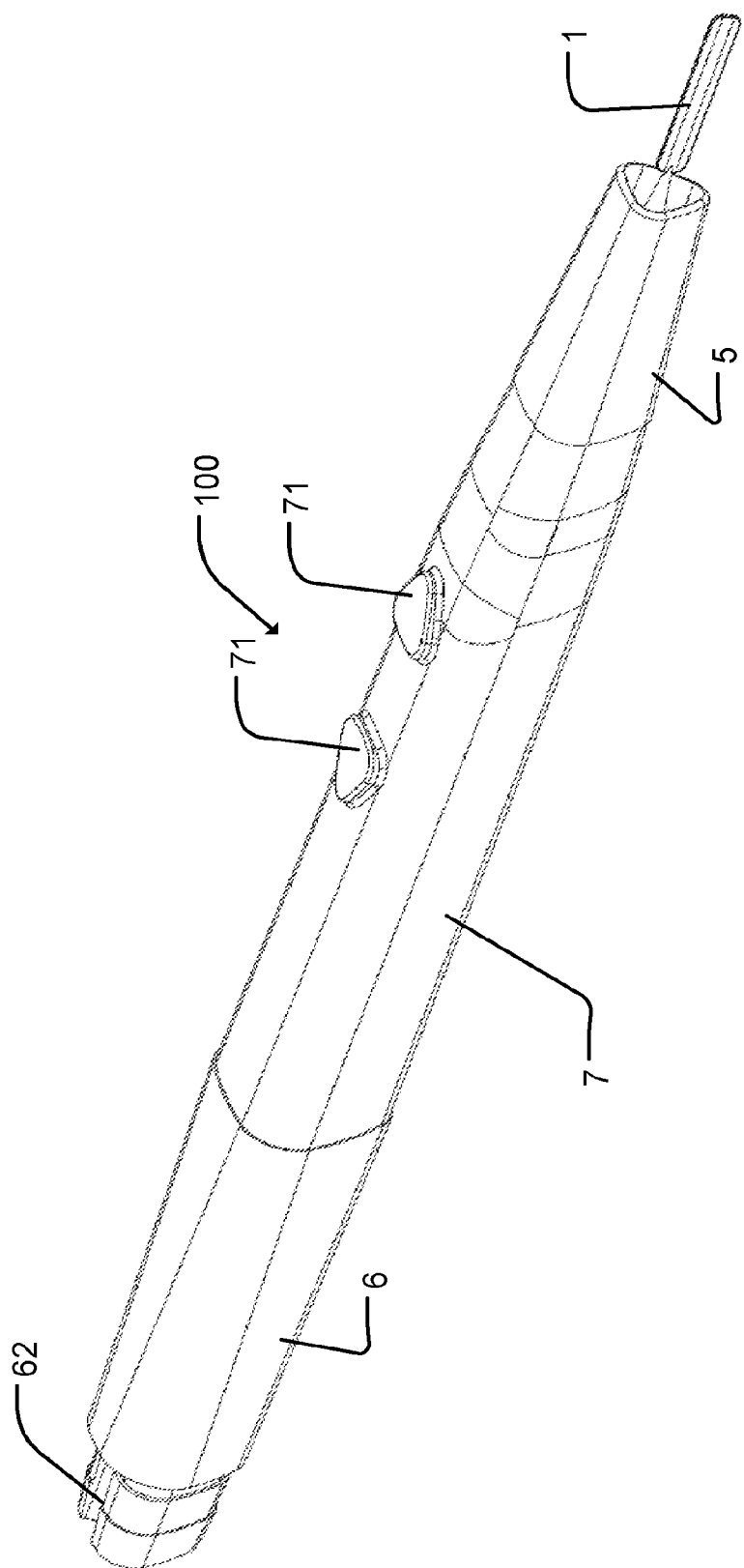
FIG. 1 is a perspective view of an electrosurgical pencil according to the invention.
Figure 2:
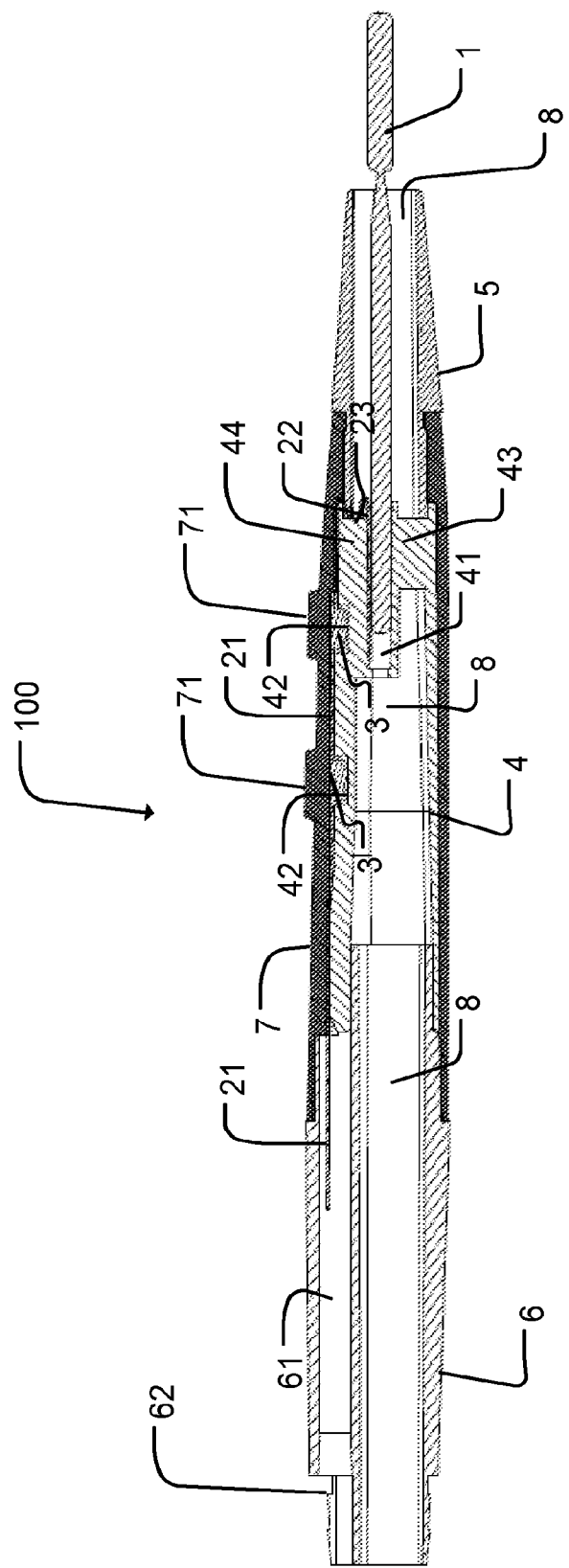
FIG. 2 is a vertical cross sectional lengthwise view.
Figure 3:
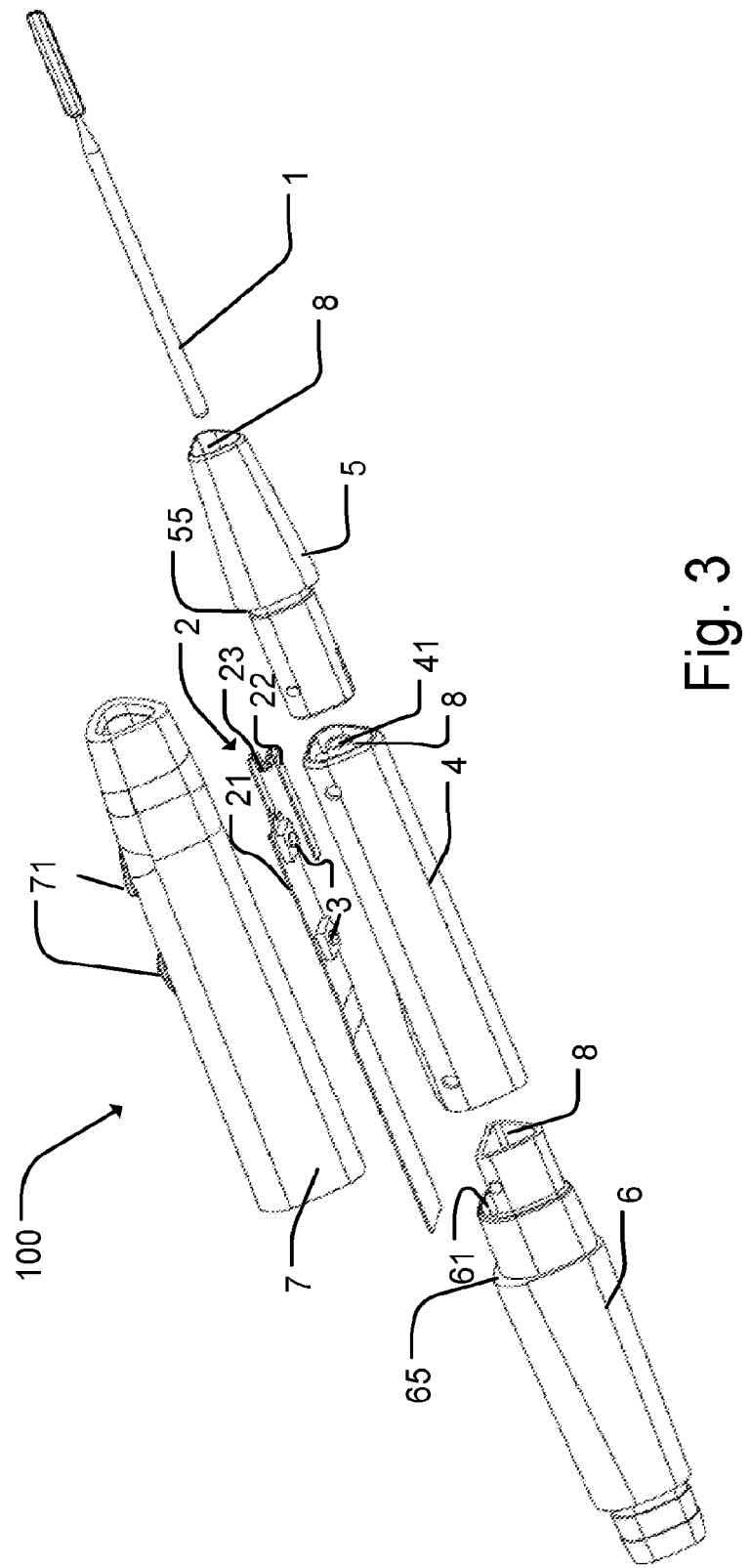
FIG. 3 is an exploded view of an electrosurgical pencil according to the invention.
Figure 19A:
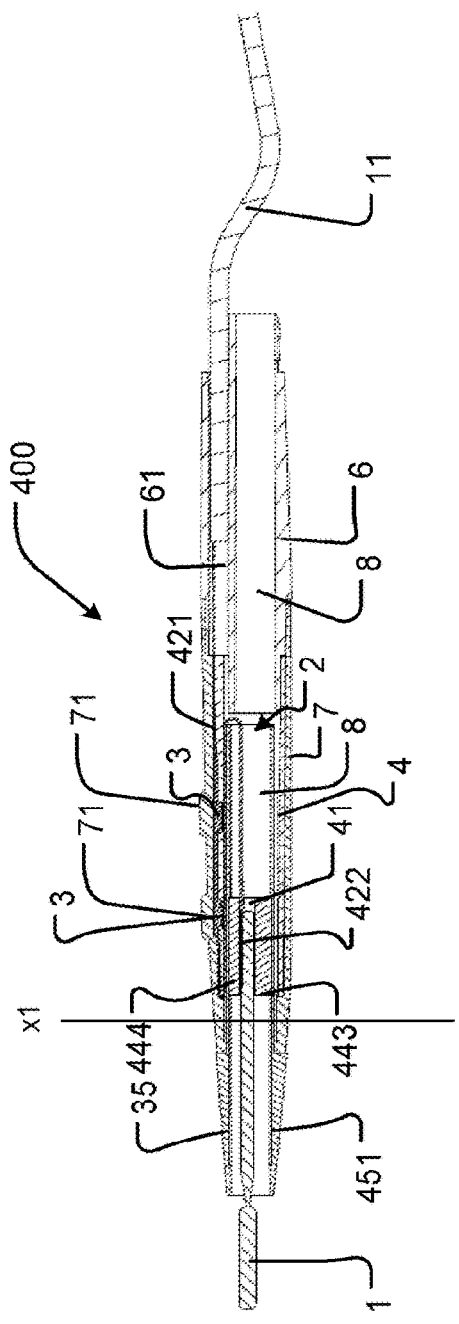
Figure 19B:
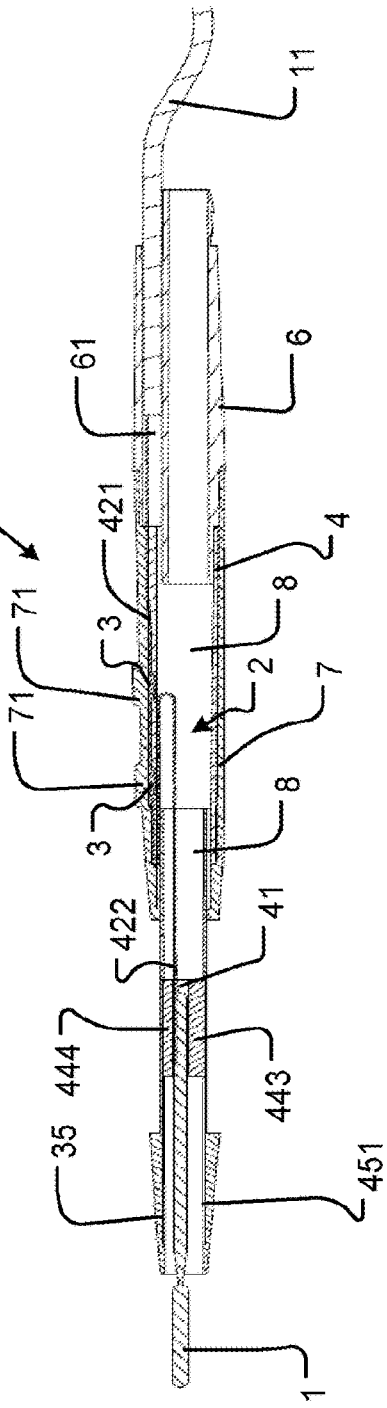
Figure 19C:
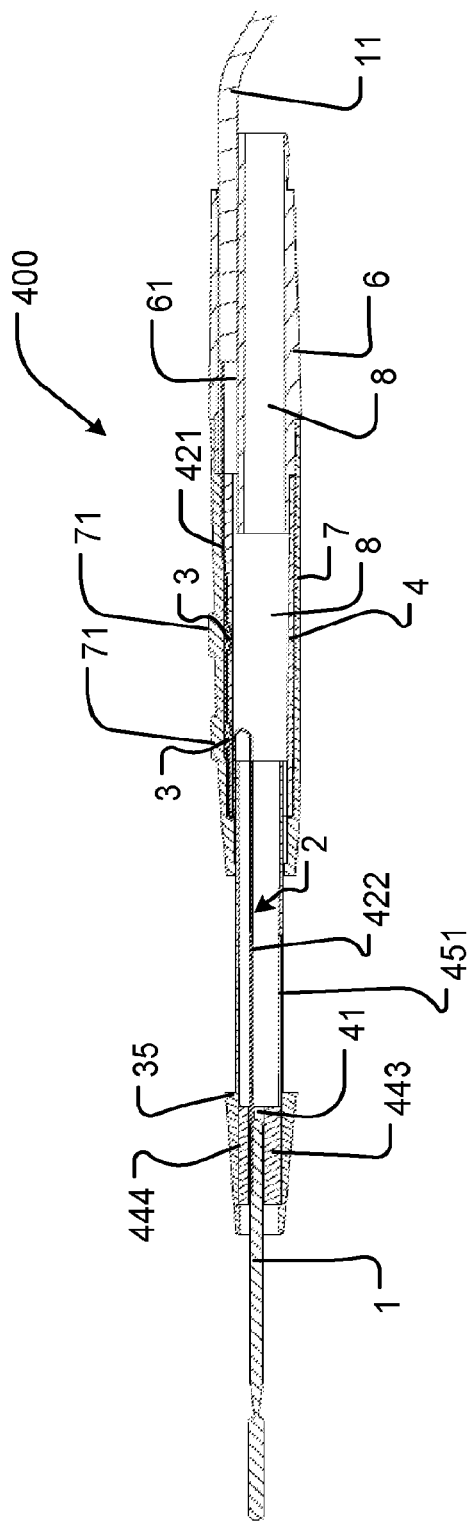

FIGS. 19a-c show a third embodiment of the electrosurgical pencil 400 in a non-extended position and in a position with an extended first housing part and in a position with an extended electrode 1, respectively. What differs from the embodiment in FIG. 2 is that the flexible printed circuit 2, comprising a first portion 421 and a second portion 422, is longer. The first housing part 35 is also longer compared to the housing part in FIG. 2. The first housing part 35 is adapted to slide inside main housing part 4, such that the user is able to telescopically to extend the pencil 400 as seen in FIG. 19b. When the user pulls the first housing part 35, the electrode 1 and the flexible printed circuit 2 will follow. The flexibility of the flexible printed circuit 2 is used such that the flexible printed circuit 2 remains in contact with both the electrode 1 and the switching means 3. The pencil 400 is provided with a locking means (not shown) such that it may be impossible to pull the first housing part 35 completely out of the pencil 400.

Because the sheath 7 is made of silicone or a similar material, there is friction between the first housing part 35 and the sheath 7, which keeps the first housing part 35 in position during use. Another means for creating friction between the two may be used. Friction means may also be provided between the main housing part 4 and the first housing part 35.

In addition to the above mentioned differences the electrosurgical pencil 400 further differs from the embodiment in FIG. 2 in that it is provided with sliding means making possible to extend the electrode 1 from the first housing part 35 as seen in FIG. 19c. The sliding means 451, 443 can clearly be seen in FIG. 19d. This feature is particularly useful when the surgeon is operating in deep cavities. The first housing part 35 is provided with sliding means comprising a guide 451. The first housing part 35 accommodates an element, which element comprises the support member 443 and 444 and the receiving means 41 for holding the electrode 1. The sliding means also comprises a support member 443, which is adapted to slide in the guide 451. The extension of the electrode 1 is accomplished by pulling the electrode 1, which remain in the receiving means 41 and in contact with the flexible printed circuit 2 while being extended from the first housing part 35. In order to detach the electrode 1 from the receiving means 41, the electrode 1 must be turned first.

A cross section of the embodiment of the electrosurgical pencil 400 can be seen in FIGS. 19d and 19e. The cross section in FIG. 19e is indicated on FIG. 19a by the line X1-X2.

Like parts in each of the several figures are identified by the same reference. Any feature from any embodiment may be combined with each other independently of other features and no feature is essential unless explicitly mentioned in the claims. When referring to a pen, pencil or electrosurgical pencil, we are referring to an electrosurgical pencil.

What is claimed is:

1. Extendable electrosurgical pencil (400) adapted to receive an electrode (1) controllable by an electrical signal for performing surgical operations, comprising:
   a housing that comprises a first housing part (35) and a second housing part (6), and a main housing part (4) between the first housing part (35) and the second housing part (6),
   a flexible printed circuit (2),
   switching means (71) on the main housing part (4) of the housing and being adapted to be activated from outside the housing for closing the flexible circuit (2), and
   the first housing part (35) comprises receiving means (41) for receiving the electrode, wherein the first housing part (35) is adapted to slide inside the main housing part (4) to provide a telescopic extension of the pencil (400), the electrode (1) and the flexible printed circuit (2) following the sliding movement.

2. Electrosurgical pencil (400) according to claim 1, wherein the first housing part (35) of the electrosurgical pencil (400) has sliding means (451,443) to telescopically extend the electrode (1) from the first housing part (35).

3. Electrosurgical pencil (400) according to claim 2, wherein the sliding means comprises a guide (451) and a support member (443), which is adapted to slide in the guide (451).

4. Electrosurgical pencil (400) according to claim 3, wherein the first housing part (35) accommodates an element, which element comprises the support member (443) and (444) and the receiving means (41) for holding the electrode (1).

5. Electrosurgical pencil (400) according to claim 2, wherein extension of the electrode (1) is accomplished by pulling the electrode (1), which remain in the receiving means (41) and in contact with the flexible printed circuit (2) while being extended from the first housing part (35).

6. Electrosurgical pencil (400) according to claim 1, wherein the flexible printed circuit (2) is of a paper-thin flexible material having a control structure printed upon it, wherein the flexible printed circuit (2) remains in contact with both the electrode (1) and the switching means (3).

7. Electrosurgical pencil (400) according to claim 6, wherein the paper-thin flexible material is a foil.

8. Electrosurgical pencil (400) according to claim 1, wherein the electrosurgical pencil (40) is provided with a locking means such that the first housing part (35) cannot be pulled completely out of the electrosurgical pencil (400).

9. Electrosurgical pencil (400) according to claim 8, wherein the sheath has a thickness that is greater than 0.35 mm in the area of the switching means.

10. Electrosurgical pencil (400) according to claim 1, wherein the switching means (3,71) comprises a switch (3) and an actuator (71).

11. Electrosurgical pencil (400) according to claim 10, wherein the first portion of the flexible printed circuit (21) is positioned between the actuator (71) and the switch (3).

12. Electrosurgical pencil (400) according to claim 1, wherein the electrosurgical pencil (400) further comprises a suction channel along the length in the interior of the pencil (400).

13. Electrosurgical pencil (400) according to claim 1, further comprising friction means between the main housing part (4) and the first housing part (35).

14. Electrosurgical pencil (400) according to claim 1, further comprising a sheath (7) that encloses the main housing part (4).

15. Electrosurgical pencil (400) according to claim 14, wherein the sheath (7) is made of a material that provides friction between the first housing part (35) and the sheath (7), which keeps the first housing part (35) in position during use of the electrosurgical pencil (400).

16. Electrosurgical pencil (400) according to claim 14, wherein the sheath (7) is made of silicone.

17. Electrosurgical pencil (400) adapted to receive an electrode (1) controllable by an electrical signal for performing surgical operations, comprising:
   a housing that comprises a first housing part (35) and a second housing part (6), and a main housing part (4) between the first housing part (35) and the second housing part (6), a flexible printed circuit (2),
   switching means (71) on the main housing part (4) of the housing and being adapted to be activated from outside the housing for closing the flexible circuit (2), and
   the first housing part (35) comprises a receiving means (41) for receiving the electrode, wherein the first housing part (35) is adapted to slide inside the main housing part (4) to provide a telescopic extension of the pencil (400), the electrode (1) and the flexible printed circuit (2) following the sliding movement, and wherein the flexible printed circuit comprises a first portion (21) and a second portion (22), wherein the second portion (22) is folded substantially parallel to the first portion (21), when mounted in the housing, wherein the second portion of the flexible printed circuit (22) extends into the receiving means (41) of the housing.

18. Electrosurgical pencil (400) adapted to receive an electrode (1) controllable by an electrical signal for performing surgical operations, comprising:

a housing that comprises a first housing part (35) and a second housing part (6), and a main housing part (4) between the first housing part (35) and the second housing part (6), a flexible printed circuit (2), switching means (71) on the main housing part (4) of the housing and being adapted to be activated from outside the housing for closing the flexible circuit (2), and the first housing part (35) comprises a receiving means (41) for receiving the electrode, wherein the first housing part (35) is adapted to slide inside the main housing part (4) to provide a telescopic extension of the pencil (400), the electrode (1) and the flexible printed circuit (2) following the sliding movement, and wherein the exterior of the electrosurgical pencil (400) has a substantially triangular shape defined by the area ratio between a first triangle (310) which circumscribes said substantially triangular shape and a second triangle (320) inscribed in said substantially triangular shape, is between 1:1 and 3:1.

19. Electrosurgical pencil (400) according to claim 18, wherein at least one corner (340) of the substantially triangular shape (330) has a radius of curvature that is between 1 mm and 5 mm or that is between 2 mm and 4 mm.

* * * * *